US011633618B2

(12) United States Patent
Gangwish et al.

(10) Patent No.: US 11,633,618 B2
(45) Date of Patent: *Apr. 25, 2023

(54) MUSCLE OPTIMIZATION DEVICE AND METHOD

(71) Applicant: Genovus Biotechnolgies Inc., Louisville, CO (US)

(72) Inventors: Kimberly S. Gangwish, Louisville, CO (US); Garret Moddel, Boulder, CO (US); Casey Zahorik, Louisville, CO (US)

(73) Assignee: Genovus Biotechnologies Inc., Louisville, CO (US)

(*) Notice: Subject to any disclaimer, the term of this patent is extended or adjusted under 35 U.S.C. 154(b) by 215 days.

This patent is subject to a terminal disclaimer.

(21) Appl. No.: 17/130,829

(22) Filed: Dec. 22, 2020

(65) Prior Publication Data

US 2021/0128931 A1    May 6, 2021

Related U.S. Application Data

(63) Continuation of application No. 15/269,693, filed on Sep. 19, 2016, now Pat. No. 10,888,707, which is a
(Continued)

(51) Int. Cl.
*A61N 2/00* (2006.01)
*A61N 2/02* (2006.01)
(Continued)

(52) U.S. Cl.
CPC .......... *A61N 2/002* (2013.01); *A61N 2/008* (2013.01); *A61N 2/02* (2013.01); *A61N 7/00* (2013.01);
(Continued)

(58) Field of Classification Search
CPC .... A61H 23/00; A61H 23/008; A61H 23/004; A61H 23/02; A61H 23/0236;
(Continued)

(56) References Cited

U.S. PATENT DOCUMENTS 4,364,378 A   12/1982   Seuss et al.
5,131,401 A    7/1992   Westenskow et al.
(Continued)

FOREIGN PATENT DOCUMENTS

WO   2007005582 A1   1/2007
WO   2008088985 A2   7/2008
(Continued)

OTHER PUBLICATIONS

European Search Report dated Feb. 9, 2017 in European Application No. 15765096.1.
(Continued)

*Primary Examiner* — Colin W Stuart
(74) *Attorney, Agent, or Firm* — Berg Hill Greenleaf Ruscitti LLP

(57) ABSTRACT

A system, device and method are provided for exposing a patient to therapeutic resonant frequency patterns (RFP) for therapy and treatment of a patient, for example, biological tissue such as muscle, tendon, ligament, and nerve tissue. The resonance frequencies originate from many bioactive substances, pharmaceuticals or other compounds, and key frequencies of the RFP of a compound can be replicated and then delivered to a patient using an electromagnetic catalyst to provide therapeutic benefits. RFPs can be imprinted in a separate device using a plasma imprinting device and method. This separate device can be actively excited by a delivery mechanism that uses electromagnetic or mechanical waves to interact with the device. The actively excited device transmits the RFPs or therapeutic resonant frequency
(Continued)

patterns to the patient for similar enhancements and therapeutic benefits.

18 Claims, 14 Drawing Sheets

Related U.S. Application Data continuation-in-part of application No. PCT/US2015/021554, filed on Mar. 19, 2015, and a continuation-in-part of application No. PCT/US2015/050695, filed on Sep. 17, 2015, and a continuation-in-part of application No. 14/490,378, filed on Sep. 18, 2014, now Pat. No. 10,322,063, which is a continuation-in-part of application No. 14/219,623, filed on Mar. 19, 2014, now abandoned.

(60) Provisional application No. 61/803,395, filed on Mar. 19, 2013.

(51) Int. Cl.
*A61N 7/00* (2006.01)
*A61B 5/00* (2006.01)
*A61N 1/04* (2006.01)
*A61N 1/36* (2006.01)
*H05H 1/24* (2006.01)
*H05H 1/46* (2006.01)

(52) U.S. Cl.
CPC ............ *A61B 5/4519* (2013.01); *A61B 5/486* (2013.01); *A61B 5/4848* (2013.01); *A61N 1/0452* (2013.01); *A61N 1/36003* (2013.01); *H05H 1/2443* (2021.05); *H05H 1/4652* (2021.05)

(58) Field of Classification Search
CPC .... A61H 39/00; A61H 39/002; A61H 39/007; A61H 2039/005; A61H 99/00; A61N 7/00; A61N 2007/0021; A61N 2007/0026; A61N 2007/0004; A61N 2007/0073; A61N 2/00; A61N 2/002; A61N 2/006; A61N 2/02; A61N 2/004; A61N 1/00
See application file for complete search history.

(56) References Cited

U.S. PATENT DOCUMENTS

| | | | |
|---|---|---|---|
| 5,393,350 | A | 2/1995 | Schroeder |
| 5,597,976 | A | 1/1997 | Schroeder |
| 5,651,973 | A | 7/1997 | Moo-Young et al. |
| 5,759,198 | A | 6/1998 | Karell |
| 6,033,531 | A | 3/2000 | Brooks et al. |
| 6,132,452 | A | 10/2000 | Pinter |
| 6,148,822 | A | 11/2000 | Cron et al. |
| 6,424,864 | B1 | 7/2002 | Matsuura |
| 6,425,851 | B1 | 7/2002 | Klontke |
| 6,475,514 | B1 | 11/2002 | Blitzer et al. |
| 6,558,695 | B2 | 5/2003 | Luo et al. |
| 7,035,691 | B2 | 4/2006 | Campos |
| 7,175,587 | B2 | 2/2007 | Gordon et al. |
| 8,145,318 | B2 | 3/2012 | Van Herk |
| 8,265,763 | B2 | 9/2012 | Fahey |
| 8,315,711 | B2 | 11/2012 | Campos et al. |
| 10,888,707 | B2 * | 1/2021 | Gangwish ............... A61N 7/00 |
| 2002/0031814 | A1 | 3/2002 | Brooks et al. |
| 2002/0072501 | A1 | 6/2002 | Cyr et al. |
| 2002/0156340 | A1 | 10/2002 | Blendemann |
| 2003/0118615 | A1 | 6/2003 | Blendermann |
| 2004/0059218 | A1 | 3/2004 | Kanda et al. |
| 2004/0162583 | A1 | 8/2004 | Bingham et al. |
| 2006/0084891 | A1 | 4/2006 | Barthe et al. |
| 2006/0100549 | A1 | 5/2006 | Schultheiss et al. |
| 2006/0206108 | A1 | 9/2006 | Hempel |
| 2006/0239928 | A1 | 10/2006 | Heit et al. |
| 2007/0219470 | A1 | 9/2007 | Talish et al. |
| 2008/0233308 | A1 | 9/2008 | Mosaico |
| 2008/0281238 | A1 | 11/2008 | Oohashi et al. |
| 2008/0288035 | A1 * | 11/2008 | Gill ......................... A61N 2/02 607/108 |
| 2009/0103066 | A1 | 4/2009 | Butler et al. |
| 2009/0118816 | A1 | 5/2009 | Kipshidze et al. |
| 2009/0254008 | A1 | 10/2009 | Shields, Jr. |
| 2009/0293907 | A1 | 12/2009 | Fung et al. |
| 2010/0015918 | A1 | 1/2010 | Liu et al. |
| 2011/0073462 | A1 | 3/2011 | Brooks et al. |
| 2011/0184356 | A1 | 7/2011 | Schmidt |
| 2012/0245483 | A1 | 9/2012 | Lundqvist |
| 2012/0323149 | A1 | 12/2012 | Chou |
| 2014/0187851 | A1 | 7/2014 | Cetroni |
| 2014/0200487 | A1 | 7/2014 | Ramdas et al. |
| 2014/0288471 | A1 | 9/2014 | Gangwish et al. |

FOREIGN PATENT DOCUMENTS

| | | |
|---|---|---|
| WO | 2012116038 A2 | 8/2012 |
| WO | 2012160549 A2 | 11/2012 |
| WO | 2014006598 A1 | 1/2014 |

OTHER PUBLICATIONS

Efthimiou, et al., "Complementary and alternative medicine use in rheumatoid arthritis: proposed mechanism of action and efficacy of commonly used modalities", Rheumatol International, 2010, vol. 30, pp. 571-586.

Ke, et al., "Intluenece of Electromagnetic Signal of Antibiotics Excited by Low-Frequency Pulsed Electromagnetic Fields on Growth of *Escherichia coli*", Cell Biochemistry and Biophysics, 2013, vol. 67, pp. 1229-1237.

Lappin, et al., "Effects of a Pulsed Electromagnetic Therapy on Multiple Sclerosis Fatigue and Quality of Life: A Double-Blind, Placebo Controlled Trial", Alternative Therapies, 2003, vol. 9(4), pp. 38-48.

Psaltis, et al., "Holographic Memories", Scientific American, 1995, vol. 273(5), pp. 70-76.

International Search Report and Written Opinion for International (PCT) Patent Application No. PCT/US2014/031221, dated Sep. 4, 2014, 7 pages.

International Search Report and Written Opinion for International (PCT) Patent Application No. PCT/US2015/021554, dated Jun. 25, 2015, 10 pages.

International Preliminary Report on Patentability for International (PCT) Patent Application No. PCT/US2014/031221, dated Oct. 1, 2015, 6 pages.

International Search Report and Written Opinion for International (PCT) Patent Application No. PCT/US2015/050695, dated Dec. 18, 2015, 9 pages.

* cited by examiner

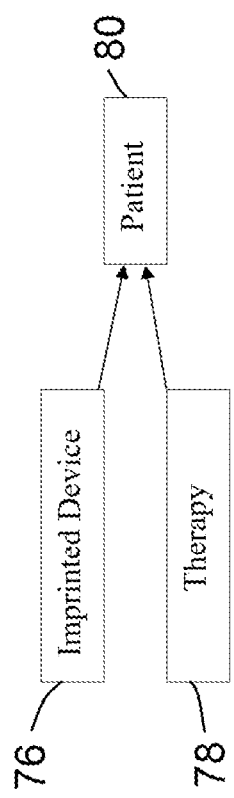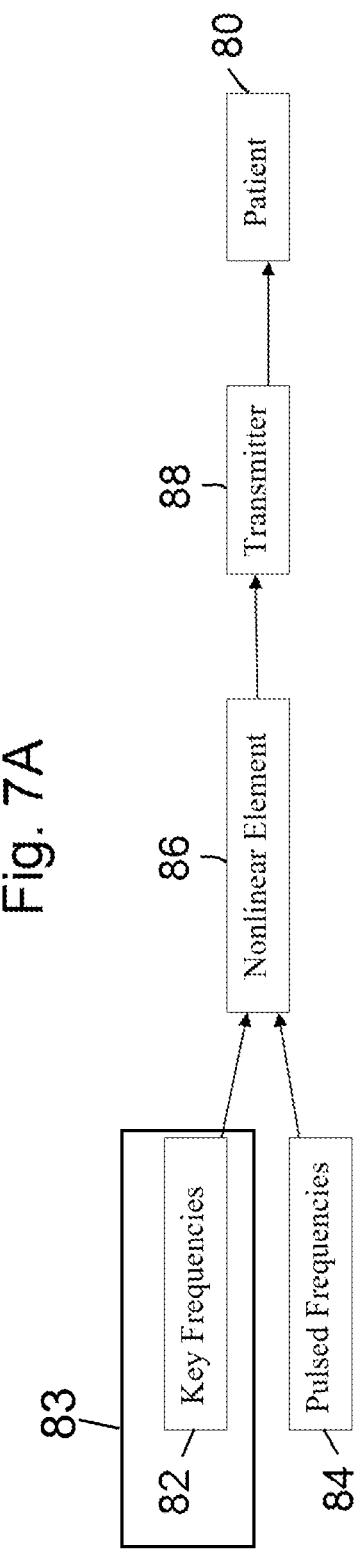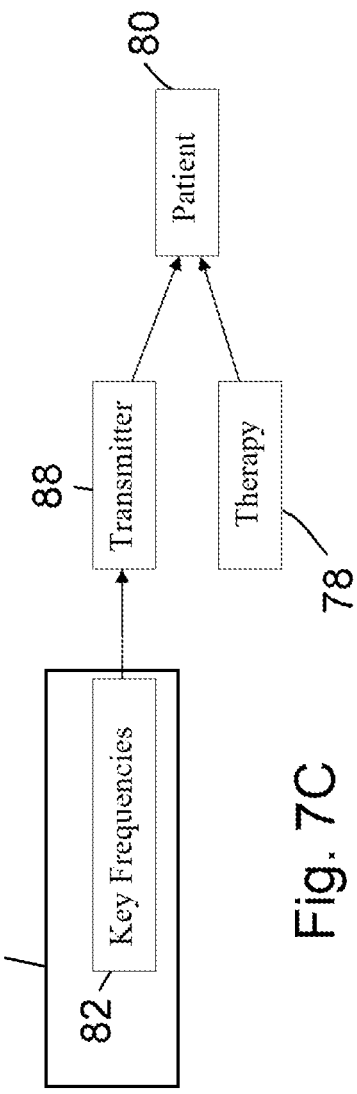
Fig. 7A
Fig. 7B
Fig. 7C

MUSCLE OPTIMIZATION DEVICE AND METHOD

CROSS REFERENCE TO RELATED APPLICATION

This application is a continuation of U.S. application Ser. No. 15/269,693, filed Sep. 19, 2016, which is a continuation-in-part of PCT Application No. PCT/US2015/021554, filed Mar. 19, 2015. The U.S. application Ser. No. 15/269,693, filed Sep. 19, 2016 is also continuation-in-part of PCT Application No. PCT/US2015/050695, filed Sep. 17, 2015. The U.S. application Ser. No. 15/269,693, filed Sep. 19, 2016 is also a continuation-in-part of U.S. application Ser. No. 14/490,378, filed Sep. 18, 2014, which is a continuation-in-part of U.S. application Ser. No. 14/219,623, filed Mar. 19, 2014, which claims the benefit of U.S. Provisional Application No. 61/803,395, filed Mar. 19, 2013, all of which are incorporated herein in their entirety by reference.

FIELD OF THE INVENTION

The present invention relates generally to the field of muscle stimulation, and more particularly, to therapy and treatment of muscle, tendon, ligament, and nerve tissue by use of a device and method in which tissues and associated proprioceptors and neuromuscular feedback loops are exposed to therapeutic resonant frequency patterns (RFPs), and/or the RFPs are transmitted to a patient.

BACKGROUND OF THE INVENTION

Stimulation and exercise of muscle tissue is necessary for the rehabilitation and continued development of damaged and/or poorly functioning muscle tissue. The failure to stimulate and exercise muscle tissue inevitably results in muscle atrophy, and long periods of muscle inactivity can result in permanent damage.

There are a number of existing devices and methods that are used for muscle stimulation and rehabilitation, primarily in the field of neuromuscular electrical stimulation (NMES). NMES is known to provide many therapeutic benefits such as prevention or retardation of disuse atrophy, pain relief, improvement of blood circulation, and others. Most forms of electrical stimulation involve the delivery of intermittent and repeating series of electrical pulses to the targeted muscle tissue(s). In many systems, the pulses are delivered transcutaneously by surface electrodes that are placed on the patient's skin over the targeted muscle area(s).

Included within this body of knowledge regarding LAMES are a number of patent references. One example includes the U.S. Pat. No. 8,265,763. This reference discloses systems and methods for neuromuscular electrical stimulation. Stimulation electrodes are provided on a stimulation pad, configured to provide electrical stimulation to a targeted tissue. A system for neuromuscular electrical stimulation also includes a pressure generating mechanism to provide a compressive force to a region of the targeted tissue, thereby removing excess fluid from the region.

Another example of a US patent reference includes the U.S. Pat. No. 8,315,711. This reference discloses a method and apparatus using resonant pulses to treat diabetes, carpal tunnel syndrome, arthritis, and other maladies by applying a stimulating signal to promote and manipulate blood flow. The stimulating signal may include a resonant sequence that includes at least three pulses, where the pulses of the resonant sequence are spaced relative to one another such that each pulse subsequent to a first pulse in the sequence is effective to progressively stimulate and create tension in a musculature that includes the muscle inwardly from the electrodes and towards the center of the musculature, while maintaining the tension created in at least a portion of the musculature by each preceding pulse in the resonant sequence.

Yet another example of a US patent reference that discloses an invention in this field is the U.S. Pat. No. 8,145,318. This reference generally discloses an apparatus for electrical stimulation of muscle tissue, including an electrode system with an electrode array. The array has a plurality of electrode pads and is placed in electrical contact with the targeted muscle tissue. The electrode system further includes a sensor for sensing a property of the muscle tissue. This property forms a measure for the activity of the muscle tissue. The apparatus includes an electrode selector for selecting one or more stimulating electrode pads. A signal generator is connected to the electrode array for providing an electrical stimulation signal to the stimulation electrode pad. A signal processor is connected to the sensor for determining from the sensor signal a value of the muscle activity, and outputting the value to a human perceptible form. This reduces the accuracy required to position the electrode system and increases the accuracy of measuring muscle tissue activity.

Another example of a US patent reference includes the U.S. Pat. No. 7,175,587. This reference discloses an apparatus and method for using pulsed electromagnetic field (PEMF) to provide a therapeutic benefit. This reference describes inducing a magnetic field in a biological system where the pulsed electromagnetic field is used for therapeutic treatment of injury, illness, and/or aging. A straight wire element generates an electromagnetic field in response to a current pulse through the straight wire element, and a circuit that supplies the current pulse does so using a square pulse. This allows the PEMF device to generate an electromagnetic field with rapid rise and fall times and to provide the desired therapeutic benefit.

As further background, it is helpful to understand basic muscle physiology. Muscle fibers are activated when an alpha motor neuron (which extends from the spinal cord to the muscle) is activated. Each alpha motor neuron activates a unique set of individual muscle fibers in what is called a "motor unit." The amount of force that a muscle can generate is directly related to the number of motor units that are activated. During muscle testing, if the subject can resist the amount of pressure applied, then the muscle has been activated isometrically and no change in joint position is noted. However, if the muscle cannot resist the amount of force applied, the muscle will lengthen in what is called an eccentric contraction and there is a change in joint position or angle.

Whether or not a subject can resist the pressure applied during muscle testing depends on many factors, both excitatory and inhibitory. In other words, the level of activation of the alpha motor neuron depends on complex interactions between neurons in the spinal cord. One of the major factors that influences alpha motor neuron activity is the effect of feedback from the muscle spindle and the Golgi Tendon Organ (GTO). The muscle spindle and GTO are sensory organs located within the muscle and tendon, respectively, and provide rich information about the length of the muscle and the amount of force produced by the muscle. For example, when a muscle is stretched, all the muscle fibers are lengthened, including the muscle spindles. The muscle spindle signals the change in the length of the muscle and activates the 1a sensory nerve that communicates the change to the spinal cord. The activation of the 1a nerve can cause activation of the alpha motor neuron of the same muscle (the agonist), and inhibit the activation of the opposite muscle (the antagonist). Similar principles can be applied to groups of muscles, whether antagonistic or synergistic. The GTO registers the amount of muscle force, but may also inhibit force production if there is a possibility of muscle damage at high forces. Inputs on the alpha motor neurons can also come from supraspinal areas of the cerebral cortex, cerebellum, or brainstem or reflexes.

Together these sensors that sense position, length, and tension of muscles are called "proprioceptors". The feedback from these sensors, which are actually specialized nerve endings, goes entirely to the spinal column and subconscious parts of the brain, e.g. spinal segments, brainstem, basal ganglia, thalamus, cerebellum, etc. This provides the body with information on the state of muscle contraction, muscle and tendon tension, position and activity of joints, and equilibrium. When stimulated, many of these proprioceptors adapt quickly and provide information on instantaneous change and rate of change in muscle activity and body position. Others adapt only slowly to stimulation and therefore provide steady-state information about muscle and body position. Working together they provide the information necessary for coordinated muscle action and movement and the maintenance of posture.

All muscles in the body with few exceptions are arranged in antagonistic pairs of muscles. This arrangement of muscles can be referred to as reciprocal facilitation/inhibition, because whenever one of the pair is facilitated or turned on, its antagonist (or antagonists as there may be several) is automatically inhibited or turned off. Hence, the turning on and turning off are both normal states of muscle function. When a muscle contracts isometrically during muscle monitoring, signals are sent to the "prime mover" (PM) to hold the position of the body part by consciously facilitating the PM. Then as the pressure on the body part (e.g. an arm held horizontal) is increased during muscle monitoring, the muscle sensors (muscle spindle) in the PM respond by a spinal reflex arc referred to as the "load reflex". The load reflex increases the degree of PM contraction, while at the same time inhibiting their antagonists and facilitating their synergists. Synergists are muscles that help the PM in holding the arm up, but are not in their position of optimal mechanical advantage. Synergists contribute much less than the PM to establishing and maintaining this position. A muscle circuit can be defined as the PM and all other muscles, both synergists and antagonists, to which it is "wired" both at the level of the brain and spinal reflex arcs.

FIG. 1 provides an example of a simplified muscle circuit. More specifically with respect to a muscle circuit, each muscle in the body has antagonists (usually more than one) that oppose its action. The agonist or PM and its antagonist(s) are neurologically wired together via the spindle cells in the belly of these muscles. This neurological wiring is such that when a PM is facilitated (turned on) it sends signals to automatically inhibit (turn off) its antagonist(s) to the same degree it has been facilitated. At the same time, if the load is sufficiently large it facilitates its synergists. In this way, the limb moves in the direction of contraction, unopposed by its antagonist(s), permitting smooth and rapid movement of the limb. Likewise, facilitation of an antagonist will inhibit the PM, as the spindle cells of the antagonist(s) need to inhibit the PM in order to move the limb in the opposite direction from the action of the PM. Referring to FIG. 1, it illustrates a muscle circuit consisting of an agonist or prime mover (biceps), one antagonist (triceps) and one synergist (brachioradialis). The spindle cell of the PM is wired to both its antagonist, which it inhibits, and its synergist, which it facilitates. Not shown is the reciprocal spindle cell circuitry for the antagonist, the triceps. When the triceps is facilitated, spindle cells in the belly of the triceps send signals to inhibit the biceps and its synergists the brachioradialis.

During a series of muscle contractions and relaxations, information on this series of activity is also sent to subconscious parts of the brain, e.g. the basal ganglia and thalamus, which control "pre-recorded" muscle programs, and the cerebellum where comparisons are made of intended actions and actual actions. If an intended action is to keep the arm held at horizontal, but the arm moves downward due to the increasing pressure of a dynamic load, the subconscious brain centers augment the automatic spinal load reflex and orders additional contraction of the PM to offset movement, thereby helping the arm to remain horizontal. As long as the flow of information from muscle sensors to and from the brain remains "clear" with no interruptions, the muscle can maintain the isometric contraction until the muscle reaches its full power of contraction. If loading continues above this point, the arm will move down as the PM is overpowered by the downward pressure of the dynamic load, resulting in an eccentric contraction.

During muscle testing, the pressure applied is far less force than needed to overpower the PM. A muscle with full neurological integrity should therefore maintain the isometric contraction during muscle monitoring. That is, unless something interferes with the neurological flow of information between the muscle and the central nervous system, the muscle should be facilitated sufficiently to maintain its physical position even under increasing load. This capability of the muscle to maintain an isometric contraction indicates a muscle that can be considered in "balance" with its neurological circuitry. If there is interference or a disruption in the flow of information between a muscle and the central nervous system, the muscle will not be able to coordinate and match its degree of facilitation to the increasing loading taking place during muscle testing/monitoring. Accordingly, the arm will move downward appearing to fail under the monitoring pressure, resulting in an eccentric contraction. A muscle that fails to maintain the isometric contraction such as by inhibited feedback from muscle spindle cells, tendon and joint sensors or inhibitory feedback from subconscious emotional brain centers, can be described as being "under-facilitated" relative to the pressure being applied. The eccentric contraction of the muscle may be observed simply as the muscle being weak (i.e. failing under the monitoring pressure). However, the muscle is not weak, but rather inhibited or under-facilitated to resist the monitoring pressure.

For muscles to function properly, they require a number of different nutrients, including vitamins, minerals, and trace elements in sufficient concentrations to maintain the required energy production for muscle function. Muscle tissue also requires a variety of amino acids for structural integrity and repair, and to provide energy for proper muscle function. When any of the components of this nutritional formula is deficient, it may reduce the effectiveness of muscle function. Additionally, the proper ratios and concentrations of the nutrients within this formula are necessary for maintenance of on-going muscle function. One of the problems of aging is a decrease in the effectiveness with which the body both assimilates and utilizes nutrients and thus muscle function is often affected by these nutrient imbalances due to these natural processes.

While there may be a tremendous amount of information available regarding traditional techniques and therapies for improving muscle function, the great majority of this information relates to electrical or chemical methods of treatment. Muscle stimulation by NMES has proven to provide certain benefits. Providing a patient with an improved diet and/or supplementation of vitamins, minerals, and other nutrients that were shown to be lacking has also proven to provide certain benefits.

However, nutritional supplementation, stimulation and exercise alone are often not enough to strengthen "weak" muscles due to inhibition of the muscle via muscle spindle cell, Golgi tendon organ and Golgi ligament organ receptors whose job it is to "protect" the structural integrity of the muscle and its related tendons and ligaments should tension on the muscle exceed a threshold level. Often injury or even simply slipping or an unusual activity can "unset" this threshold for inhibition such that the Spindle cell, Golgi tendon organ or Golgi ligament organ receptors now inhibit the muscle action long before there is any likelihood of damage to the muscle, tendon or ligament. Thus, when the person now tries to use this muscle it appears "weak" as it just cannot develop much power.

A muscle in this "inhibited" state responds very poorly to normal rehabilitation even using the electrical stimulating devices because according to Wolf's Law in physiology, in order to build more strength, and muscle must develop more tension. This is because tension is the signal for the muscle to make more muscle fibers, which is what increases its strength. If, however, the muscle is inhibited at a specific level of tension (even one that does not approach tension that would be harmful) by the "unset" Spindle cell, Golgi tendon or Golgi ligament organ receptors, this inhibition prevents the development of further tension, and thus the muscle is not given the signal to make more muscle fibers. Muscles inhibited in this way, even when exercised regularly can never get stronger, and thus present as chronic muscle problems. Until the "unset" receptors are "reset", this problem will persist.

Thus, traditional techniques and therapies for improving muscle function still may not provide optimal results for many patients that have certain imbalances or maladies manifesting in poor muscle function. In addition, traditional delivery platforms for medical treatments such as hypodermic injections, oral ingestion, or dermal patches have shortcomings. Namely, traditional delivery platforms are indiscriminate and result in many negative side effects. Therefore, there is still a need to provide an alternative form of treatment and delivery platform that does not rely upon traditional techniques/therapies.

SUMMARY OF THE INVENTION

In accordance with the present invention, a device and method are provided that expose a patient to therapeutic resonant frequency patterns (RFP). This delivery platform addresses shortcomings of traditional delivery platforms such as negative side effects, and therapeutic RFPs can be used for therapy and treatment of biological tissue such as muscle, tendon, ligament, and nerve tissue. In addition to musculature treatments, a device and method are provided that can expose all or portions of the body to compounds to induce a response from the body. Disease states that may be treated or ameliorated using the devices and methods of the present invention include multiple sclerosis, Parkinson's disease, cerebral palsy, amyotrophic lateral sclerosis (Lou Gehrig's Disease, ALS), muscular dystrophy, myotonic dystrophy, and Graves' disease, spinal-bulbar muscular atrophy, myasthenia gravis, Huntington's Disease, polymyositis, Lambert-Eaton syndrome, monomelic amyotrophy, progressive bulbar palsy, lower motor neuron weakness, upper motor neuron weakness, peripheral neuropathy, diabetic peripheral neuropathy, spinal cord injuries, botulism, Guillain Barre syndrome, and Pompe disease. Devices and methods of the present invention may also be used in coordination with rehabilitation, physical and occupational therapy, osteopathic and chiropractic treatment, and sports training.

According to the present invention, it may be considered a device and method in which tissues and associated proprioceptors and neuromuscular feedback loops are exposed to therapeutic RFPs and/or therapeutic RFPs are transmitted to, or interact with, a patient, in which the RFPs originate from many types of bioactive substances or domains, including vitamins, minerals, herbs, amino acids, proteins, nucleic acids, fatty acids, nutritional supplements, and pharmaceutical compounds. The particular combination of the bioactive substances or domains used in the present invention is designed to achieve a specific effect and may be referred to as a "muscle formula", a "hypoxic formula", or any other formula as explained further below. Each formula includes nuclear magnetic resonance (NMR) spectrum or infrared vibrational (IV) spectrum based on, for example, the physical properties of constituent substances. These frequency-based properties as transferred to the device of the invention are artifacts of the formula, and can be referred to as RFPs.

The RFPs of a formula are identified, captured, and ultimately delivered or transferred to a device or patient. To identify the RFPs of a formula through IV spectrum, an infrared spectrometer such as a Fourier transform infrared spectrometer outputs a series of absorption lines as a function of the wavenumber, which is proportional to the inverse of the wavelength. The largest absorption lines correspond to the characteristic vibration modes of atoms with the formula of interest. The most significant of these absorption lines are chosen by a standard (e.g., the largest two to five absorption lines), then an arbitrary waveform generator can reproduce the absorption lines to replicate key frequencies of the RFP of the formula. The NMR of a formula may be similarly utilized to replicate key frequencies of the RFP of a formula. See Verginadis, I. I., Simos, Y. V., Velalopoulou, A. P., Vadalouca, A. N., Kalfakakou, V. P., Karkabounas, S. C. & Evangelou, A. M., Analgesic effect of the electromagnetic resonant frequencies derived from the NMR spectrum of morphine, Electromagnetic Biology and Medicine, 31(4): 275-284, 2012. The replicated key frequencies of the RFP of a formula have been applied to chemical systems as described in U.S. Pat. No. 6,033,531; US Publication No. 2011/0073462; and US Publication No. 2002/0031814.

The process or means by which the NMR spectrum are delivered or transferred to a device or patient can be described as methods of transfer by imprinting, infusing, entraining, or imaging. As used hereinafter, the terms "transfer", "imprint" or "imprinted" as used hereinafter can describe the each or selected ones of these methods of transfer and/or the physical state of the device of the invention after transfer of the RFPs. The imprint of the RFPs is a durable and lasting condition for the device that may last months or even years.

The targeted muscle or tissue of a patient has various ways to receive RFPs delivered from a device. All molecules, including biologically-active molecules, store energy in a wide range of modes (including electronic, vibrational, rotational, and nuclear magnetic energy states), and exchange it with the environment via resonant frequencies spanning a correspondingly large range of the electromagnetic spectrum (from ultraviolet, visible and infrared light through microwaves, radio waves, and possibly even extremely low frequencies). Energy exchanged via higher-energy interactions is typically quickly dispersed in dense media as heat, though metastable low-energy states can persist for extended periods of time. There is evidence that cellular chemistry and intra- and inter-cellular communication and signaling can be affected by electromagnetic stimuli in these energy regimes.

According to one theory, the human body may respond directly to the frequencies or molecular resonance of bioactive substances including, but not limited to, nutrients, hormones, neurotransmitters, neuropeptides, and cytokines. Such a response might be mediated by sympathetic resonance, which does not require actual contact of the substances with the body. An analogy is the tuning-fork effect, in which a first tuning fork, vibrating at its resonance frequency, will cause another tuning fork of the same frequency to vibrate at the same frequency, even though there is no direct physical contact between the tuning forks (in this case, in air, the resonance is mediated by pressure waves in the acoustic medium). Via a corresponding phenomenon, molecular resonance might transfer energy between similar molecules or similar molecular subunits, even when they are not touching. The manner in which resonant frequencies mediate interactions among nutrients and other molecules within the body is a topic of current research.

A recent study conducted in the United Kingdom involved research on how molecules interact via their emitted or radiated frequencies. This study evolved from successful treatments of people with electromagnetic sensitivity. In the study, clinical data supported a conclusion that a chemical in a sealed vial or ampoule can trigger an allergic reaction, for example, without the substance being introduced into the patient's body or touching their body. Thus, a reasonable mechanism to explain these phenomena is that the molecules in the sealed vial when placed near the body transmit their specific frequencies to the body via the weak electromagnetic fields that they emit, which in turn interacts with the resonance frequencies of molecules within the body. See Choy, R. V. S., Monro, J. A. and Smith, C. W., Electrical Sensitivities in Allergy Patients; Clinical Ecology 4(3): 93-102, 1987; see also Smith, C. W., Electromagnetic Effects in Humans; In Biological Coherence and Response to External Stimuli, Herbert. Froelich (ed.) Springer-Verlag, Berlin, pp. 205-232, 1988.

Another study examined the effect of exposure of rats to electromagnetic waves related to the RFP of morphine. Rats exposed to these electromagnetic waves showed decreased nocioception (sensitivity to pain stimuli) compared to rats exposed to nonspecific frequencies, rats exposed both to morphine-specific frequencies and a morphine suppressor, and a control group, though the decrease was not as great as for rats treated with morphine by injection. See Verginadis, I. I. et al.

In summary, the frequencies radiated by the molecules as well as the chemicals themselves can disrupt regulatory systems, or restore these systems to normal operation. These phenomena fall into the category of external or exogenous homeopathy in which the remedy does not touch the body, yet produce a specific physiological effect, e.g. an allergic reaction, or the elimination of an allergic reaction. This provides a model for how the RFPs of the nutrients in the muscle formula may be transmitted to the tissues of the muscles, tendons, ligaments, and nerves, and that this exposure can bring the muscle back into normal function, even when the device of the present invention is not physically touching the body or placed directly on the muscle being treated.

Some embodiments the present invention incorporate a device or substrate of a suitable material upon which the therapeutic RFPs of a formula are imprinted. Suitable materials include, but are not limited to, glasses, ceramics, minerals, plastics, semiconductors, and piezoelectric materials, in pure, mixed and doped forms, with crystalline, polycrystalline, glassy, amorphous, or sintered structure.

Similarly; in another preferred embodiment, an imprinted material may be applied to or embedded within a device. The material may include a liquid, gel, or slurry containing a formula mixed with an adhesive glue. As mentioned, the formula may include, but is not limited to, sodium, magnesium, calcium, potassium, boron, chloride, sulphate, bicarbonate, alumina, and silica, and combinations thereof. The material is mixed with adhesive glue that may be applied to the device.

Also in accordance with the preferred embodiment, the RFPs of a formula may be embedded within the device. First, the formula is prepared by grinding and mixing the constituent components of the formula. Listed below are chemicals/compounds/plant types that may be used within the formula. These chemicals/compounds/plant types may be used in different quantities and/or concentrations within the formula to achieve specific objectives for the treatment to be conducted. Although a specific listing of components is provided, it should be understood that the formula can incorporate a host of other components, and therefore Phis listing should not be considered as exclusive. These components may include

| | |
|---|---|
| L-Phenylalanine | Choline |
| L-Glutamine | Lecithin |
| L-Carnitine | Calcium gluconate |
| L-Taurine | Magnesium stearate or gluconate |
| Betatene or other mixed carotenoids | Silica |
| Magnesium stearate or gluconate | Iron gluconate, picolinate or glycinate |
| Lemon or citrus bioflavonoids | Zinc gluconate or picolinate |
| Lithium | Manganese gluconate |
| Thiamine (Vitamin B1) | Chromium sulphate or picolinate |
| Riboflavin (Vitamin B2) | Potassium iodide |
| Nicotinamide (Vitamin B3) | Minerals |
| Calcium pantothenate (Vitamin B5) | D-Ribose |
| Pyridoxine (Vitamin B6) | Hyaluronic acid |
| Methylcobalamin (Vitamin B12) | Chondroitin sulphate |
| Folic acid or L-Methylfolate | Glycosylated glucosamine |
| Biotin | Collagen |
| | Creatine monohydrate |
| Ascorbic acid (Vitamin C) | Kelp |
| Rosehips | Alfalfa, |
| Vitamin D | White Willow Bark Extract, |
| Vitamin E (preferably, d-alpha) | and combinations of these components. |
| Inositol | |

The lithium may include organic sources of lithium, such as lithium found in brewer's yeast (*Saccharomyces cerevisiae*), or lithium in mineral form (e.g. *lithium orotate*).

The D vitamin may be supplied as vitamin D3 (cholecalciferol) and/or vitamin D2 (ergocalciferol).

The minerals may include any elements selected from: Ag, Al, As, Au, B, Ba, Be, Bi, Br, C, Ca, Cd, Ce, Cl, Co, Cr, Cs, Dy, Er, Eu, F, Ga, Gd, Ge, H, Hf, Hg, Ho, I, In, Ir, K, La, Li, Lu, Mg, Mn, Mo, N, Na, Nb, Nd, Ni, O, Os, P, Pb, Pd, Pr, Pt, Re, Rh, Ru, S, Sb, Sc, Se, Si, Sm, Sn, Sr, Ta, Tb, Te, Th, Ti, Tl, Tm, V, W, Y, Yb, Zn, and Zr. Preferably, these minerals are used or added to other components of the muscle formula as a colloidal suspension.

Lemon bioflavonoids are anthoxanthins (flavones and flavonols) that may include isoflavonoids derived from 3-phenylchromen-4-one (3-phenyl-1,4-benzopyrene) and neoflavonoids, derived from 4-phenylcoumarine (4-phenyl-1,2-benzopyrone). The collagen proteins may be type I or type II, or a combination thereof. Alfalfa, also called lucerne, may include flowering plants in the pea family Fabaceae. Kelps include any genera of brown algae, Phaeophyceae, in the order Laminariales.

Another embodiment of the invention is a composition comprising at least two components making up the muscle formula, including L-phenylalanine, L-glutamine, L-carnitine, L-taurine, betatene, lemon bioflavonoids, lithium, thiamine (vitamin B1), riboflavin (vitamin B2), nicotinamide (vitamin B3), calcium pantothenate (vitamin B5), pyridoxine (vitamin B6), methylcobalamin (vitamin B12), folic acid, biotin, ascorbic acid (vitamin C), rosehips, vitamin D, vitamin E (preferably, d-alpha), inositol, choline, lecithin, calcium gluconate, magnesium stearate, silica, iron gluconate, zinc gluconate, manganese gluconate, chromium sulphate, potassium iodide, minerals, D-ribose, hyaluronic acid, chondroitin sulphate, glycosylated glucosamine, collagen, creatine monohydrate, kelp, alfalfa and combinations of these components. These compositions may be dissolved or suspended in an alcohol, such as an aqueous alcohol solution. In certain embodiments, the alcohol of these compositions is ethanol.

After preparation of the formula, the therapeutic RFPs of the formula can be imprinted on the device by one of several methods as described below. In many cases, the mixture is first prepared for imprinting by dissolution in an aqueous ethanol solution. In an exemplary method, a sample of the aqueous alcohol/solution is placed into a quartz chamber. The sample might contain 5-500 ml of the solution. The quartz chamber containing the solution is placed into an apparatus in which the magnetic field generated by a pulsed electromagnetic field (PEMF) device passes through the quartz chamber, to illuminate a target device. The PEMF is activated, and the target exposed for a period of time; the time-varying magnetic field serves as a carrier wave to transfer the RFPs of the formula to the device. The RFPs has been shown to be retained or imprinted on the device.

The foregoing describes some embodiments by which therapeutic RFPs can be imprinted within a suitable material or device. The present invention encompasses other devices capable of retaining such imprints, and other methods of imposing the imprinted pattern. Other imprintable materials include materials such as glasses, ceramics, minerals, plastics, semiconductors, piezoelectric materials, gels and viscous materials, in pure, mixed and doped forms, with or without an associated or embedded formula, with or without surface treatments, and having crystalline, polycrystalline, glassy or amorphous structure. Other methods of imposing or imprinting a therapeutic RFP include techniques based on mechanical, acoustic or electromagnetic waves, and plasma generation systems, and any combination of individual techniques.

According to the method of the present invention, the RFPs of the formula can be delivered to the body in many ways, including passive or active excitement of an imprinted device. According to a first method, the imprinted device may be applied directly to the body for a period of time, while the person performs certain activities that activate specific muscles involved in different patterns of motor activity, thereby re-integrating muscle dysfunction. According to this method, the device may be applied directly over the targeted group of muscles to be treated, and then directed exercises are performed to achieve the therapeutic effect. For example, this direct application method can be achieved by placing the device on the skin over the affected muscle (such as a bicep muscle), and then the bicep muscle is taken through three series of contractions. The targeted muscle(s) are then directed to be held in their most contracted position for approximately 5 seconds while a load is applied to the body part that is supported by the targeted muscle(s). The targeted muscle(s) are then relaxed for a period of approximately 30 seconds, and the targeted muscle(s) is then directed to be isometrically contracted or locked for approximately another 5 seconds, while increasing pressure is applied against the isometrically contracted or locked muscle. The cycle may be repeated a third time. Through Electromyographic (EMG) testing (described below), it has been shown that this method can reset muscle proprioception. After a period of approximately 2 minutes, the integrity of muscle function can be re-checked to confirm that the muscle proprioception has been reset. If successful, the targeted muscle(s) should now isometrically contract or lock strongly against monitoring pressure, yet should be able to be sedated using spindle cell, golgi tendon organ and golgi ligament organs sedation techniques.

The RFP of the imprinted device may also be actively excited. For example, a device imprinted with the RFPs of a formula may be placed proximate to a muscle or muscle group of a patient. The imprinted device is excited to transmit the RFPs of the formula from the imprinted device to the muscle. Thus, for example, if the formula includes various pharmaceutical compounds, then the muscle produces a response as if the muscle were physically receiving the various pharmaceutical compounds by one or more conventional methods. This induced response provides a tangible and measurable therapeutic benefit to the patient that does not require the physical application or ingestion of a substance in the patient's body. Further, an imprinted device is or may be reusable, which may greatly reduce costs of treatment. In one preferred embodiment, the affected tissue is exposed to the magnetic field output of a PEMF device which first passes through an imprinted device. The affected muscle is taken through three cycles of contraction as described above to reset proprioception.

For example, in some embodiments the device is a piezoelectric crystal and the delivery mechanism imposes an electric field on the crystal which causes the crystal to change shape. When the delivery mechanism ceases to impose an electric field, the crystal reverts back to its original size and shape, and the crystal emits a resonance frequency. This resonance frequency and harmonics thereof may then be implemented to a user for therapeutic benefit. In embodiments of the present invention, the resonance frequency of a particular device may depend on its physical attributes. For example, the size of the device influences the resonance frequency. In crystals such as quartz, how the crystal is cut influences the resonance frequency. In an "AT" type of crystal cut, the crystal's x axis is inclined by approximately 35° relative to the z axis. This cut results in a crystal that is less sensitive to fluctuations in temperature. Additionally, the material that the layer is comprised from influences the resonance frequency.

According to the theory supporting the therapeutic benefits of the present invention, muscle imbalance or dysfunction can be caused by the lack of or incoherence of certain frequencies needed to maintain normal function. Direct activation or dynamic muscle activity exposes the muscle imbalance to therapeutic intervention. The device imposes a harmonic resonance field to the muscle imbalance. Thus, the affected muscle can be brought back into normal function by transferring the RFP retained in the imprinted device to the muscle, thereby resetting muscle function.

Treatment by use of the invention can be enhanced if the caregiver has a working knowledge of muscle function, including how to position muscles for proper muscle monitoring. Treatment can be further enhanced if the caregiver has a working knowledge of muscle monitoring or muscle testing techniques.

The device and method of the present invention can rapidly reset muscle proprioception to restore normal muscle function, often resolving even long-term chronic pain and dysfunction. The device and method may further reduce days of stay in a hospital, reduce rehabilitation times, reduce need for many operations, and save the hospital and insurance systems time and resources, as well as to save patients out of pocket costs. This invention is also non-invasive with only minimal side-effects. Through IRB-approved university research, it has been found that muscle improvement can take place, often within seconds up to a period of 30 minutes, and these benefits appear to be long-lasting. Therefore, embodiments of the present invention may serve as a delivery mechanism for medicine, just as capsules, syringes, IV drips, and dermal patches deliver medicine.

In view of the disclosures herein a series of five exemplary embodiments of the present invention are provided. In a first exemplary embodiment, replicated key frequencies of the RFP of a formula are imprinted or transferred to a device, or a neutral medium such as silicon, which is then positioned on or near a patient. A series of testing steps can be administered to discern the state of a portion of the body. Then, a series of therapeutic steps can be performed on the patient with the imprinted device located on or near the target portion of the body. The device catalyzes the patient's response to a PEW therapy and enables or enhances the response. It will be appreciated that any electromagnetic therapy can be used in embodiments of the invention.

The RFP of the formula sample can be identified by a nuclear magnetic resonance spectrum of the formula sample where the nuclear magnetic resonance spectrum has a plurality of local peaks, and at least one of the local peaks is selected to replicate key frequencies of the RFP of the formula sample. Alternatively, the RFP of the formula sample can be identified by an infrared vibrational spectrum of the formula sample where the infrared vibrational spectrum has a plurality of local peaks, and at least one of the local peaks is selected and frequency-shifted down to a frequency with harmonics at the infrared frequency to replicate key frequencies of the RFP of the formula sample. The combined electronic signal delivered by a transmitter can comprise a waveform, wherein the waveform is one or more of a square wave, a pulse wave, and a sawtooth wave.

In a second exemplary embodiment, a method of delivering replicated key frequencies of a RFP and a pulsed electromagnetic field frequency is provided to a patient. In this embodiment, the physical catalyst in replaced with an electromagnetic catalyst, which has multiple benefits. For instance, an electromagnetic catalyst does not wear out over time like a physical catalyst. In addition, the frequencies of an electromagnetic catalyst can easily be changed, and thus, multiple catalysts can be used in a session in a preprogrammed fashion. Further still, an electromagnetic catalyst and a PEMF device can apply electromagnetic frequencies to a common area on the patient since, in some embodiments, the frequencies of the electromagnetic catalyst and the PEMF device are emanated from the same source. This improves the effectiveness of the treatment in patients.

In practice, a formula sample having a RFP is provided, and the RFP is identified so that key frequencies of the RFP can be replicated. These replicated key frequencies of RFP of the formula sample are combined with a pulsed electromagnetic field frequency into a combined or mixed electronic signal. A transmitter such as a diode, coil, or antenna emits the combined electronic signal to an area of a patient to catalyze a response from the patient.

Frequencies can be combined or mixed by applying a voltage or current containing multiple frequencies to a nonlinear element, such as a diode. The diode output contains the original frequencies as well as sum and difference frequencies of the original frequencies. Alternatively, multiple sets of frequencies, for example catalyst and PEMF frequencies, can simply be applied simultaneously through a single coil or antenna.

In a third exemplary embodiment, another method of delivering replicated key frequencies of a RFP and a pulsed electromagnetic field frequency is provided to a patient, except that the two frequencies are provided by separate sources. A formula sample having a RFP is provided, and the RFP is identified so that key frequencies of the RFP can be replicated. A first arbitrary waveform generator is provided to generate key frequencies of the RFP and deliver these frequencies via a transmitter to a portion of the patient. A second arbitrary waveform generator is provided to generate a pulsed electromagnetic field frequency and deliver these frequencies via a transmitter to the same or different portion of the patient. In some embodiments, key frequencies of the replicated RFP of the formula sample and the pulsed electromagnetic field frequency are simultaneously delivered to the patient, and the addition of the key frequencies of a RFP to the pulsed electromagnetic field frequency serves to catalyze a patient's response to the PEMF therapy and enables or enhances the response.

It will be appreciated that the catalyzing effect can be used with a wide range of other electromagnetic therapies, such as transcranial direct current stimulation (tDCS). A further application of the invention is to enhance the effectiveness of non-electromagnetic therapies, including pharmaceuticals, physical and chiropractic therapy, homeopathy, acupuncture, psychological counseling, and traditional approaches such as Qigong and Ayurvedic medicine.

In a fourth exemplary embodiment, a device is imprinted with key frequencies of a RFP of a formula sample by a plasma generator and process, then the device is used to catalyze a patient's response to a PEMF treatment. The plasma generator may comprise a vessel that defines an enclosed volume where the enclosed volume has a first end and a second end. The enclosed volume has a formula area positioned between the first end and the second end. An inert gas source is operably interconnected to the first end of the enclosed volume of the vessel, and a pump is operably interconnected to the second end of the enclosed volume of the vessel. Examples of inert gases include helium, neon, argon, krypton, xenon, and radon. It will be appreciated that many other gases, and/or combinations of gases, may be used in embodiments of the invention including non-oxidizing gases, oxygen, hydrogen, nitrogen, etc. An electromagnetic field generator having a coil with at least one turn positioned about the formula area of the enclosed volume. A formula sample is at least partially provided in the formula area of the enclosed volume, and the device to be imprinted is positioned between the formula area and the second end of the enclosed volume. The pump draws air out of the enclosed volume until a pressure in the enclosed volume is below a first predetermined threshold. Then, the inert gas source releases inert gas into the enclosed volume until the pressure in the enclosed volume rises from below the first predetermined threshold to above a second predetermined threshold. The electromagnetic field generator and coil generate an electromagnetic field to strike the inert gas in the enclosed volume and produce a plasma, which imprints a RFP of the formula sample to the device.

In various embodiments, the first predetermined threshold is approximately 115 mTorr, and the second predetermined threshold is approximately 170 mTorr. In some embodiments, the inert gas is argon, and the device is a doped glass. It will be appreciated that the glass may be doped with, for example, chromium, neodymium, erbium, thulium, ytterbium, and/or other materials. It will be further appreciated that piezoelectric materials can be used in addition or in place of doped glass, as it is described herein.

In various embodiments, the electromagnetic field is activated for 15 minutes, the electromagnetic field generator generates the electromagnetic field using an electronic signal having a frequency of 13.56 MHz, and the electronic signal produced by the function generator is a waveform, wherein the waveform is one or more of a square wave, a pulse wave, and a sawtooth wave. The electromagnetic field generator may comprise multiple components. For instance, the electromagnetic field generator may comprise a function generator and an amplifier that has the coil with at least one turn positioned about the formula area of the enclosed volume, wherein the function generator is configured to transmit an electronic signal to the amplifier at a first voltage, and the amplifier outputs the electronic signal to the coil at a second voltage, wherein the second voltage is larger than the first voltage. In addition, the electromagnetic field generator may comprise an impedance matcher that is operably connected to the function generator and the amplifier, wherein the impedance matcher matches an impedance of the function generator and an impedance of the amplifier. As with other embodiments, the imprinted device is placed proximate to a patient and used in combination with other frequencies generated by, for example, a PEMF device to catalyze a patient's response to the PEMF treatment.

In a fifth exemplary embodiment, a device is imprinted by the plasma generator and process described herein. However, in contrast to the fourth embodiment described above, the fifth exemplary embodiment utilizes an additional device and method to actively excite the imprinted device. A delivery mechanism may produce two types of waves to excite the device: electromagnetic waves and mechanical waves such as acoustic waves. These waves interact with attributes of the device such that the device produces the RFP.

A further application of the invention is to enhance the effectiveness of therapeutic activities, such as exercise, meditation, tai chi, and sports practice. A further application of the invention is to enhance the effectiveness of mental activities, such as studying, practicing music playing, and carrying out presentations.

It will be appreciated that wherever a PENH is used, other radiant sources may be substituted for it, such as a laser, or a continuous electromagnetic source. Similarly; the NMR spectrum may be replaced by any other spectrum that identifies key electromagnetic or vibrational signatures of the substance. For example, the infrared vibrational spectrum may be used instead. The type of spectrum used will dictate the method used to replicate the key frequencies during therapy. While an arbitrary waveform generator that drives an antenna or coil can be used with the NMR signals, single or multiple laser lines may be used to reproduce the key frequencies in an infrared vibrational spectrum that are frequency-shifted down to a frequency with harmonics at the infrared frequencies. When a nutraceutical is described, it may be replaced by one or a combination of the multiple other materials listed in the earlier patent application.

In the cases where a coil is used, it is generally meant to be a standard coil consisting of wire wrapped in a single direction. Alternatively, a caduceus coil may be utilized, which is wound in both directions. A caduceus coil does not produce a conventional magnetic field, but rather a reduced magnetic field relative to a standard PEMF field, and some patients find such PEMF magnetic fields to be objectionable or even harmful in the case of electronic implants.

One specific embodiment of the invention is a method of delivering replicated key frequencies of a resonant frequency pattern and delivering a pulsed electromagnetic field frequency to a patient, comprising (i) providing a formula sample having a resonant frequency pattern; (ii) identifying a frequency-based characteristic of the resonant frequency pattern of the formula sample; (iii) selecting a plurality of key frequencies from the frequency-based characteristic of the resonant frequency pattern for replication; (iv) providing an arbitrary waveform generator, a nonlinear element, and a transmitter; (v) generating, by the arbitrary waveform generator, the replicated key frequencies of the resonant frequency pattern of the formula sample; (vi) combining, by the nonlinear element; the replicated key frequencies of the resonant frequency pattern of the formula sample and a pulsed electromagnetic field frequency into a mixed electronic signal; and (vii) delivering, by the transmitter; the mixed electronic signal to a patient.

In some embodiments, the frequency-based characteristic of the resonant frequency pattern of the formula sample is a nuclear magnetic resonance spectrum of the formula sample, wherein the nuclear magnetic resonance spectrum has a plurality of local peaks, and at least one of the local peaks are selected as key frequencies of the resonant frequency pattern of the formula sample. In various embodiments, the frequency-based characteristic of the resonant frequency pattern of the formula sample is an infrared vibrational spectrum of the formula sample, wherein the infrared vibrational spectrum has a plurality of local peaks that have been frequency-shifted down to frequencies with harmonics at the infrared frequencies, and at least one of the local peaks are selected as key frequencies of the resonant frequency pattern of the formula sample.

In certain embodiments, the mixed electronic signal combined by the nonlinear element comprises a waveform, wherein the waveform is one or more of a square wave, a pulse wave, and a sawtooth wave. In further embodiments; the nonlinear element is a diode configured to combine the key frequencies and the sum and difference frequencies of the key frequencies with the pulsed electromagnetic field frequency into the mixed electronic signal. In various embodiments, a pulsed electromagnetic field device comprises the arbitrary waveform generator and the nonlinear element, and the mixed electronic signal is a pulsed electromagnetic field output that is modulated by the replicated key frequencies of the resonant frequency pattern of the formula sample.

Another particular embodiment of the invention is a method of delivering replicated key frequencies of a resonant frequency pattern to a patient to catalyze a response of the patient to a therapy, comprising (viii) providing a formula sample having a resonant frequency pattern; (ix) identifying a frequency-based characteristic of the resonant frequency pattern of the formula sample; (x) selecting a plurality of key frequencies from the frequency-based characteristic of the resonant frequency pattern for replication; (xi) providing an arbitrary waveform generator and a transmitter; (xii) delivering, by the transmitter, the replicated key frequencies of the resonant frequency pattern of the formula sample that are generated by the arbitrary waveform generator to a patient; and (xiii) applying a therapy to the patient, wherein the delivery of the replicated key frequencies of the formula sample to the patient catalyzes the response of the patient to the therapy.

In various embodiments, the frequency-based characteristic of the resonant frequency pattern of the formula sample is a nuclear magnetic resonance spectrum of the formula sample, wherein the nuclear magnetic resonance spectrum has a plurality of local peaks, and at least one of the local peaks are selected as key frequencies of the resonant frequency pattern of the formula sample. In some embodiments, the frequency-based characteristic of the resonant frequency pattern of the formula sample is an infrared vibrational spectrum of the formula sample that has been frequency-shifted down to frequencies with harmonics at the infrared frequencies, wherein the infrared vibrational spectrum has a plurality of local peaks, and at least one of the local peaks are selected as key, frequencies of the resonant frequency pattern of the formula sample.

In certain embodiments, the replicated key frequencies of the resonant frequency pattern of the formula sample generated by the arbitrary waveform generator comprise a waveform, wherein the waveform is one or more of a square wave, a pulse wave, and a sawtooth wave. In additional embodiments, the formula sample is a composite formula that comprises at least one resonant frequency pattern from at least one of a nutraceutical formula; an oxygen formula, and a hypoxic formula.

In some embodiments, the therapy applied to the patient is an electromagnetic therapy, which has a pulsed electromagnetic field device that delivers a pulsed electromagnetic field to the patient, and the pulsed electromagnetic field and the replicated key frequencies of the formula sample are simultaneously delivered to the patient. In various embodiments, the therapy applied to the patient is a non-electromagnetic therapy, which is one of a pharmaceutical compound, a physical and chiropractic therapy, a homeopathy, therapy, an acupuncture therapy, psychological counseling, Qigong medicine, and Ayurvedic medicine. In certain embodiments, the therapy applied to the patient is a non-electromagnetic therapy, comprising (xiv) positioning a muscle tissue of the patient having a potential imbalance in a state of contraction; (xv) confirming an indicator change in the muscle; delivering the replicated key frequencies to the patient; (xvii) again placing the muscle in a state of contraction; (xxiii) applying pressure to the muscle; and (xix sting the muscle to confirm a therapeutic effect has been achieved.

Yet another particular embodiment of the invention is a method of delivering replicated key frequencies of a resonant frequency pattern to a patient to catalyze a response of the patient to a therapy, comprising (xx) providing a formula sample having a resonant frequency pattern; (xxi) identifying a frequency-based characteristic of the resonant frequency pattern of the formula sample; (xxii) selecting a plurality of key frequencies from the frequency-based characteristic of the resonant frequency pattern for replication; (xxiii) imprinting a device with the replicated key frequencies of the resonant frequency pattern of the formula sample; (xxiv) placing the imprinted device proximate to a patient; and (xxv) applying a therapy to the patient, wherein the replicated key frequencies of the formula sample from the imprinted device catalyzes the response of the patient to the therapy.

In some embodiments, the frequency-based characteristic of the resonant frequency pattern of the formula sample is a nuclear magnetic resonance spectrum of the formula sample, wherein the nuclear magnetic resonance spectrum has a plurality of local peaks, and at least one of the local peaks are selected as key frequencies of the resonant frequency pattern of the formula sample. In various embodiments, the frequency-based characteristic of the resonant frequency pattern of the formula sample is an infrared vibrational spectrum of the formula sample, wherein the infrared vibrational spectrum has a plurality of local peaks that have been frequency-shifted down to frequencies with harmonics at the infrared frequencies, and at least one of the local peaks are selected as key frequencies of the resonant frequency pattern of the formula sample.

In certain embodiments, the therapy applied to the patient is an electromagnetic therapy, which has a pulsed electromagnetic field device that delivers a pulsed electromagnetic field to the patient, and the pulsed electromagnetic field and the replicated key frequencies of the formula sample are simultaneously delivered to the patient. In further embodiments, the therapy applied to the patient is a non-electromagnetic therapy, which is one of a pharmaceutical compound, a physical and chiropractic therapy, a homeopathy, therapy, an acupuncture therapy, psychological counseling, Qigong medicine, and Ayurvedic medicine. In some embodiments, a plasma generator imprints the device with the plurality of key frequencies from the resonant frequency pattern of the formula sample, the plasma generator comprises a vessel that defines an enclosed volume, and the plasma generator strikes an inert gas in the enclosed volume into a plasma state, which imprints the device with the plurality of key frequencies.

BRIEF DESCRIPTION OF THE DRAWINGS

FIGS. 7A-7C show additional embodiments of the invention that catalyze a response of a patient to a therapy.

DETAILED DESCRIPTION

Figure 1:
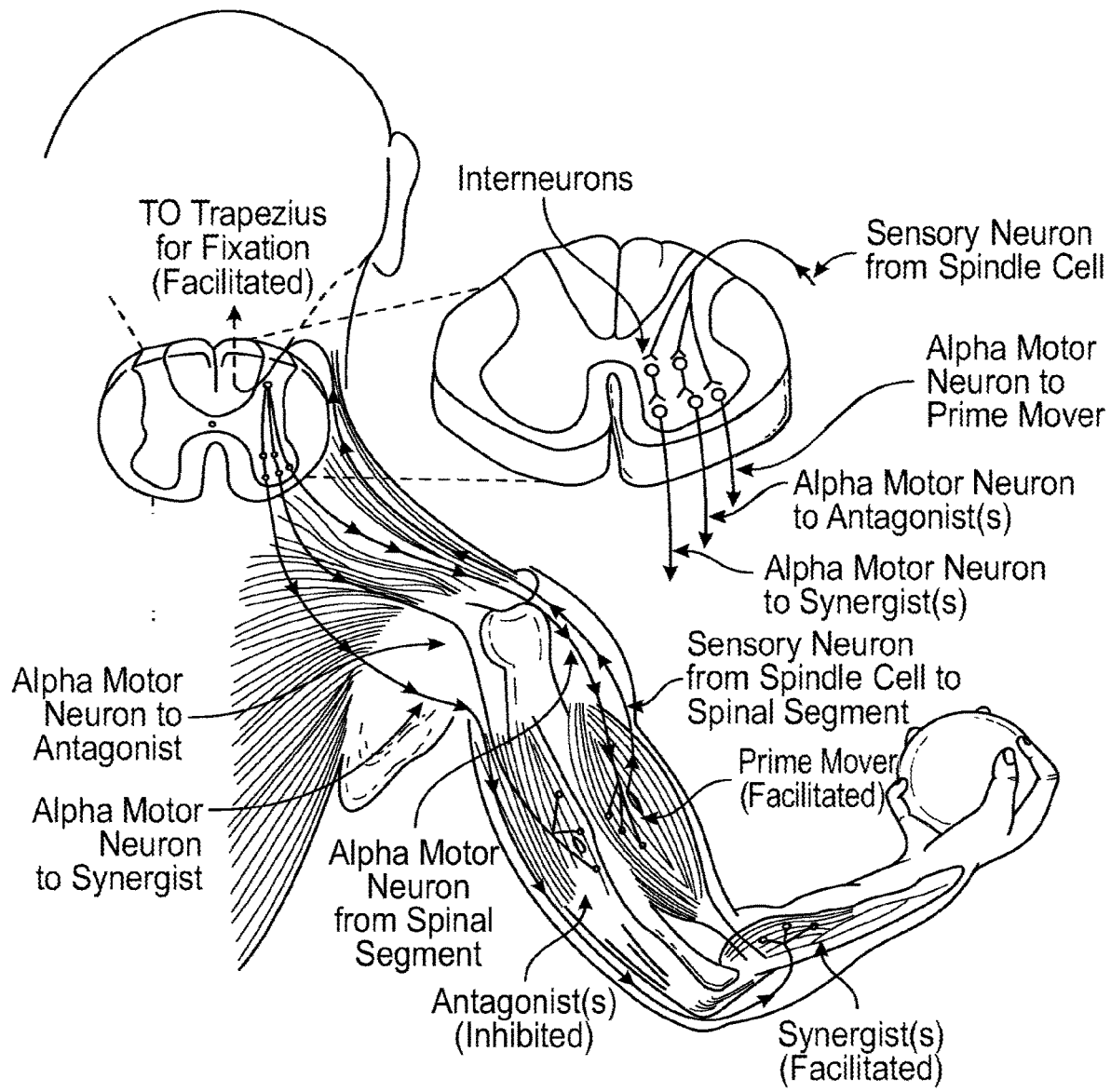
FIG. 1 is a simplified schematic diagram of muscle circuit as mentioned above.
Figure 2:
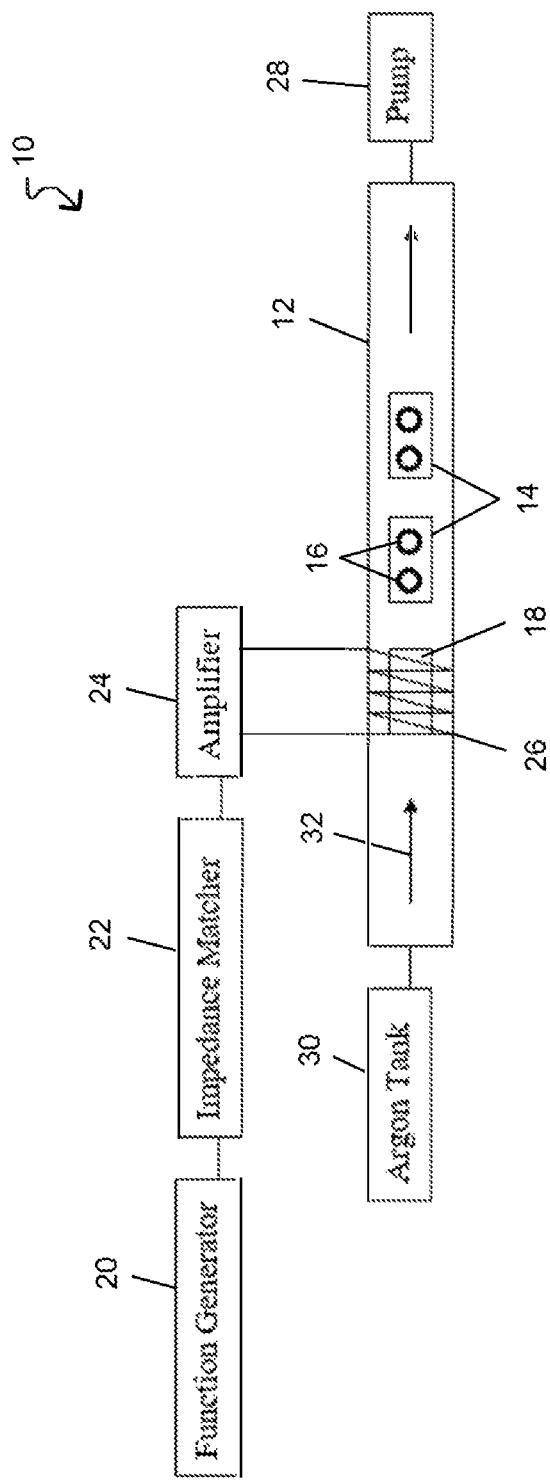
FIG. 2 is a diagram a plasma for imprinting the device of the present invention.

Referring to FIG. 2, a plasma generator system 10 is provided for imprinting doped glass or other material with the resonant frequency pattern (RFP) of a formula sample of a bioactive substance, a pharmaceutical, or other compounds. A method for using the plasma generator system 10 to imprint doped glass or other material is provided in FIG. 3. The plasma generator system 10 comprises a vessel 12 in which the target doped glass are placed. The vessel 12 in this embodiment is a hollow cylindrical tube that defines an enclosed volume. Two glass slides 14 are placed in the vessel 12, and two doped glass pieces 16 are placed on each slide. It will be appreciated that the doped glass 16 can be placed directly in the vessel 12 in some embodiments, and while the doped glass 16 may be 20 mm Swarovski glass crystals in various embodiments, the target material may not be glass. The target material may be any material capable of receiving a RFP from a formula sample.

Next, another glass slide with a formula sample 18 is positioned upstream of the glass slides 14 with the doped glass 16. Upstream in FIG. 2 is a position that is left of the glass slides 14 and doped glass 16 since an inert gas in a plasma state flows from left to right in the vessel. The formula sample 18 has a RFP, which as described herein, can be determined by the nuclear magnetic resonance spectrum, the infrared vibrational spectrum, or other frequency-based characteristics of the formula sample.

An electromagnetic field generator strikes the argon gas into a plasma state and comprises a function generator 20, an impedance matcher 22, and an amplifier 24. The function generator 20 can generate an electronic signal with a frequency between 10,000 Hz and 1000 MHz with a typical operating range between 40 kHz to 40 MHz and specific frequencies at 450 kHz, 2 MHz, 4 MHz, and 27.12 MHz. The function generator 20 in this embodiment generates an electronic signal at approximately 700 mV p-p with a frequency of approximately 13.56 MHz, which is a typical frequency for striking argon gas into a plasma state.

The impedance matcher 22 in FIG. 2 helps match the impedance between the function generator 20 and the amplifier 24 to improve the quality of the signal sent from the function generator 20 to the amplifier 24 and to maximize power transfer and/or minimize reflection between the function generator 20 and the amplifier 24. The amplifier 24 receives the electronic signal from the function generator 20 and increases the magnitude of the electric potential difference, or voltage. In the depicted embodiment, the amplifier 24 increases the voltage of the electronic signal to 80 V. The amplifier 24 outputs to a coil 26 that is wrapped around an exterior surface of the vessel 12. The coil 26 has at least one turn, and as a consequence, the amplified electronic signal from the amplifier 24 and the coil 26 produces an electromagnetic field. The area of the vessel 12 that is surrounded by the coil 26 may be referred to as a formula area, and the glass slide with the formula sample 18 may be at least partially disposed in the formula area.

Further components of the plasma generator system 10 are the pump 28 and argon tank 30. The pump 28 is used to remove the ambient air from the enclosed volume of the vessel 12, and the argon tank 30 backfills the resulting vacuum with argon gas. The electromagnetic field generator strikes the low pressure argon gas in the vessel 12 to create a plasma that imprints a RFP from the formula sample 18 to the doped glass 16. Remote plasma is used in this embodiment, however, it will be appreciated that a standard plasma may also be used in embodiments of the present invention.

Figure 3:
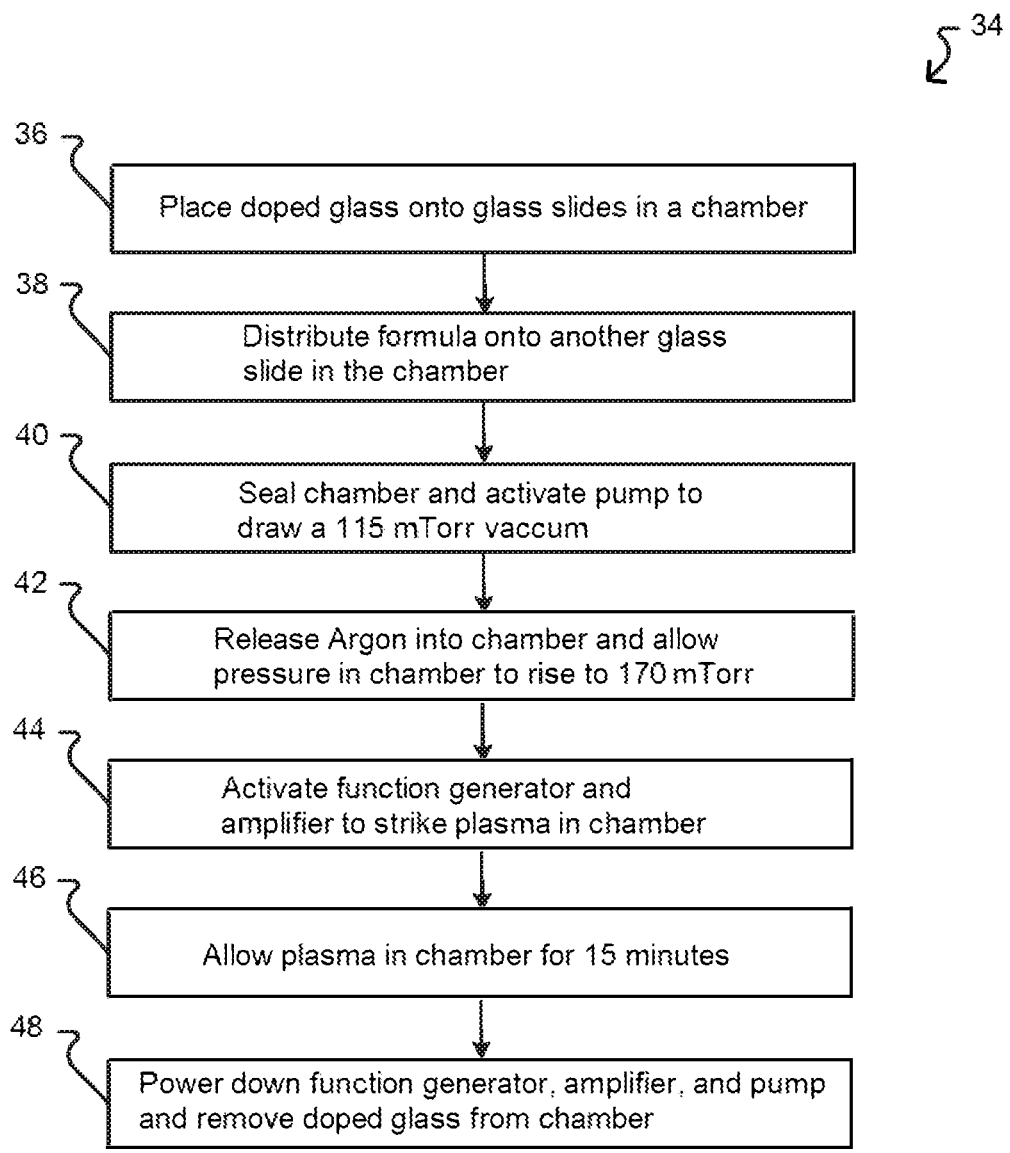
FIG. 3 is a simplified flow diagram of a method of imprinting for the device of the present invention.

Referring to FIG. 3, a method 34 of imprinting doped glass using a plasma generator system is provided. The imprinting method 34 comprises a series of exemplary steps that describe the use of an inert gas in a plasma state to imprint the RFP of a formula sample to doped glass, which can then be used to for the therapeutic benefit of a patient.

In the first step 36, doped glass is placed onto glass slides in a vessel of the plasma generator system. The doped glass is at least partially positioned in a formula area of the enclosed volume defined by the vessel so that the doped glass is subject to the electromagnetic field produced by the electromagnetic field generator.

The next step 38 is to distribute a formula sample having a RFP on the glass slide. In this embodiment, the formula sample is shaped on the glass slide so as to not impede the flow of argon gas over of the formula sample. However, it will be appreciated that in other embodiments, the shape of the formula sample, or another component of the plasma generator system, may induce turbulent flow in the vessel to increase the momentum transfer between the plasma and other components.

The vessel is sealed 40 at both ends to fully enclose the volume defined by the vessel. A pump at one end of the vessel is activated to draw the ambient air out of the enclosed volume of the vessel and produce a vacuum. The pump draws a 115 mTorr vacuum in the vessel.

Then, an argon tank at the opposite end of the vessel releases 42 the inert gas argon into the enclosed volume of the vessel, and the pressure of the vessel rises to 170 mTorr. The result is a vessel filled with low pressure argon gas. The pump and the argon gas tank can be activated during one or more steps of the method 34 to maintain a low pressure argon gas flow over the formula sample and the doped glass. The low pressure argon gas flows from the argon gas tank to the pump, and the formula sample in this embodiment is therefore upstream of the doped glass.

The electromagnetic field generator, which comprises a function generator, an impedance matcher, and an amplifier with coils around the formula area, produces 44 an electromagnetic field to strike the low pressure argon gas into a plasma state. The gas is in a plasma state in the vessel for approximately 15 minutes to imprint 46 the doped glass with the RFP of the formula sample. Once 15 minutes has expired, the various components of the plasma generator system are powered down 48. The pressure in the vessel is allowed to rise back to ambient pressure, and the doped glass in the vessel are recovered and are now imprinted with the RFP of the formula sample.

It will be appreciated that the method 34 described with respect to FIG. 2 is exemplary in nature, and the particular components and values described may vary. For example, in some embodiments, the pump may draw a vacuum down to 130 or 140 mTorr before argon is introduced to the enclosed volume to raise the pressure in the enclosed volume of the vessel to 170 or 220 mTorr. In an additional example, the amount of time that the doped glass is subjected to the plasma can be greater than or less than 15 minutes. Additionally, inert gases besides argon, and other gases capable of striking into a plasma state such as oxygen, can be used in embodiments of the present invention.

Alternatively, there are other devices and methods for imprinting a device with the RFP of a bioactive substance, a pharmaceutical, or other compounds. A device such as doped glass may be imprinted with a REP using a pulsed electromagnetic frequency (PEW) device. First, a formula is prepared, which may be a mixture of bioactive substances, and different formulas may target different physiological systems and conditions of a patient's body. For example, formulas may target muscle function (i.e., a muscle formula), tissue oxygenation (i.e., a hypoxic formula), etc. Other formulas may target neurological function, nervous system function, the digestion system, the immune system, organ function, depression, inflammation, various disease states, and other physiological systems and conditions. Formulas in some embodiments may be derived from oxygen alone or in combination with other compounds. Various bioactive substances that have a RFP may include biomolecules, cells, tissues, connective tissue, collagen (i.e. organs, bone marrow), plasma, hemoglobin, nucleic acids, DNA, RNA, enzymes, proteins, amino acids, peptides, polypeptides, carbohydrates, saccharides, lipids, signaling molecules, neurotransmitters, hormones, pheromones, immunogenic system substances, pathogens (i.e. Polio virus, malaria), nutrients, pharmaceuticals, biologics, and other biogenic substances.

Next, the formula is added to a solution, which in some embodiments is a water/ethanol mixture. It will be appreciated that while the formula may be added to a fluid, the formula may also be utilized as a solid such as a powder. In the next step, the solution is added to a chamber. In some embodiments, there is only a single chamber. However, in other embodiments, there are additional chambers, for example, two chambers, three chambers, etc. In a two chamber configuration, a second chamber may be at least partially disposed in the first chamber. The solution is located between the two chambers, and the second chamber creates a volume that is surrounded by the solution. A device or other target that is to be exposed to a wave may be placed in the second chamber.

The chamber, or chambers, may have a variety of characteristics to accommodate the process. The shape of the chamber may be any shape that defines a partially enclosed volume. For example, the chamber may have a circular cross section with an aperture at one end of the chamber configured to receive the formula. The chamber may also optionally comprise a lid to cover the aperture and fully enclose the volume. The material of the chamber may be electromagnetically transparent to allow electromagnetic waves to pass through the chamber and interact with the formula and the device. Examples of chamber materials include quartz, borosilicate glass, and inert plastics.

Next, a PENH device is placed proximate to the chamber. The PEMF device generates an electromagnetic wave with a pulse frequency or frequencies between approximately 0.5 and 50 Hz. The peak amplitude of the magnetic field generated by the PEW device may be less than 10000 gauss, and in some embodiments, the PEMF device may not generate power above a frequency of 100 kHz. A device is positioned at leak partially within the chamber, and the device is positioned such that it is opposite the PEMF device. In other words, the formula is positioned between the device and the PEMF device. The solution of formula may be characterized by optical depth, which is a dimensionless parameter that is the natural logarithm of the ratio of incident to transmitted radiant power through a material. In various embodiments, the solution through which the wave passes through has an optical depth of between approximately 0.01 and 4.

In subsequent steps, the PEMF device is activated, and the formula and the device are exposed to the PEMF's electromagnetic wave. The period of the pulse may last between approximately 2 to 600 seconds to transfer the therapeutic RFPs of the formula to the device. The resulting imprinted device may comprise only the device itself. However, it will be appreciated that in other embodiments, the device may be optionally combined with other components such as a mineral matrix layer or a protective layer, to create an imprinted device.

While a PEW device is used, other wave sources may be used to generate waves that pass through the chamber, the formula, and into the device. In one exemplary method, a sample of the aqueous alcohol/solution is placed into a Pyrex or quartz chamber. The sample might contain 5-1000 ml of the solution. One or more devices are placed within a second Pyrex or quartz container, which is placed within the first chamber so that the solution surrounds the targets. Both chambers are placed within an apparatus capable of generating oscillating electromagnetic fields. The field generator is activated, and the targets are exposed for a period of time; the oscillating electromagnetic field serves as a carrier wave to transfer the RFPs of the formula to the device. The frequency or frequencies of the electromagnetic field can vary from low through radio and microwave frequencies and combinations thereof. The RFPs have been shown to be retained or imprinted on the device.

In some embodiments, the wave source generates an electromagnetic wave having a frequency or frequencies in the range of infrared light (300 GHz-400 THz), visible light (400 THz-770 THz), and/or ultraviolet light (770 THz-30 PHz). The chamber or chambers used in these embodiments may have configurations and dimensions as discussed elsewhere herein, for example, the chamber has a portion that is optically transparent. The power of the wave source may be less than 100 W, and the period of time that the device is exposed to the wave may be between approximately 2 and 600 seconds. Other components may be utilized along the transmission path between the wave source and the chamber or chambers, including collimating lens for narrowing the wave and diverging lenses for expanding the wave.

In yet another exemplary method, a sample of the aqueous alcohol/solution is placed into a quartz chamber. The sample might contain 5-1000 ml of the solution. The quartz chamber containing the solution is placed into an apparatus in which a continuous-wave or pulsed laser passes through a beam-expanding lens and the quartz chamber, to fully illuminate a target device. The laser is activated, and the target exposed for a period of time; the laser beam serves as a carrier wave to transfer the RFPs of the formula to the device. The RFPs have been shown to be retained or imprinted on the device.

In further embodiments, the wave source generates an electromagnetic wave having a frequency or frequencies in the range of radio waves (3 Hz-300 MHz) and/or microwaves (300 MHz-300 GHz). A Gunn diode or an amplified signal generator may serve as the wave source. The peak power of the emitted waves may be less than 100 W, and the length, width, and height of the chamber may each vary between approximately 2-50 ctn. The period of time that the device is exposed to the wave may be between approximately 2 and 600 seconds.

In yet further embodiments, the wave source generates an electromagnetic wave having a frequency or frequencies in the range of low-frequency waves (below 3 kHz). A signal generator with an optional amplifier may serve as the wave source. The peak power of the emitted waves may be less than 100 W, and the length, width, and height of the chamber may each vary between approximately 2-50 cm. The period of time that the device is exposed to the wave may be between approximately 2 and 600 seconds.

In other embodiments, a magnetic source generates a magnetic field (i.e., wave) that passes through the chamber through the formula, and into the device. A first coil may be positioned at a first end of the chamber. A signal generator may supply power of less than 10 W into the first coil to directly expose the formula and the device to a magnetic field. The first coil may have a resistance of 50 ohms. In further embodiments, a second coil is positioned at a second end of the chamber, and the first and second ends may be arranged opposite each other. A third coil is positioned at a base of a second chamber, and connected via an appropriate resistance to form an electrical circuit with the second coil, and the formula is placed in the first chamber. Supplying a signal and power to the first coil induces a response in the third coil that generates a magnetic field. The length, width, and height of the chamber may each vary between approximately 2-50 cm, and the period of time that the device is exposed to the magnetic field may be between approximately 30 and 600 seconds.

In various embodiments, the wave source generates a mechanical wave such as an acoustic wave. An exemplary wave source may be a speaker with a strong frequency response below 200 Hz, and the chamber may be made from an acoustically-transparent material or have an acoustically-transparent section oriented toward the transmission path of the acoustic wave. The energy supplied to the speaker may be less than 100 W. The length, width, and height of the chamber may each vary between approximately 2-50 cm, and the period of time that the device is exposed to the magnetic field may be between approximately 2 and 600 seconds. Various waveforms may be used in conjunction with the embodiment described with respect to FIG. 2. These waveforms include those described elsewhere herein. Various embodiments may further comprise a protective cover that contains the waves transmitted through a formula and into a device. The protective covers can be made from shapes and materials that allow the protective cover to function as a Faraday cage.

A single device may be imprinted with one or more therapeutic RFPs, and there are several systems and processes to imprint a device with the therapeutic RFPs of multiple formulas. First, a device may be imprinted with therapeutic RFPs serially. In one example, the device is subjected to a wave passing through a formula, and the device is imprinted with the therapeutic RFPs associated with the formula. Then, the device is subjected to a wave passing through a hypoxic formula, and the device is imprinted with the therapeutic RFPs associated with the hypoxic formula. Thus, the resulting device is imprinted with therapeutic RFPs associated with both the formula and the hypoxic formula.

Second, the device may be imprinted with therapeutic RFPs simultaneously. This means that a composite formula may be formed from one or more constituent formulas. For example, a formula and a hypoxic formula may be combined to form a composite formula. Then, a wave passing through the composite formula imprints therapeutic RFPs on the device where the therapeutic RFPs as associated with both the formula and the hypoxic formula. The imprinting process in various embodiments may employ any wave generation processes discussed herein, including those associated with the subsequent excitation of the RFPs from the imprinted device. In addition, the imprinting methods described with respect to FIG. 2 create a first generation device. A first generation device may be excited to imprint RFPs onto another device. This second imprinted device is a second generation device. The process may be continued to create any number of generation devices.

Figure 4A:
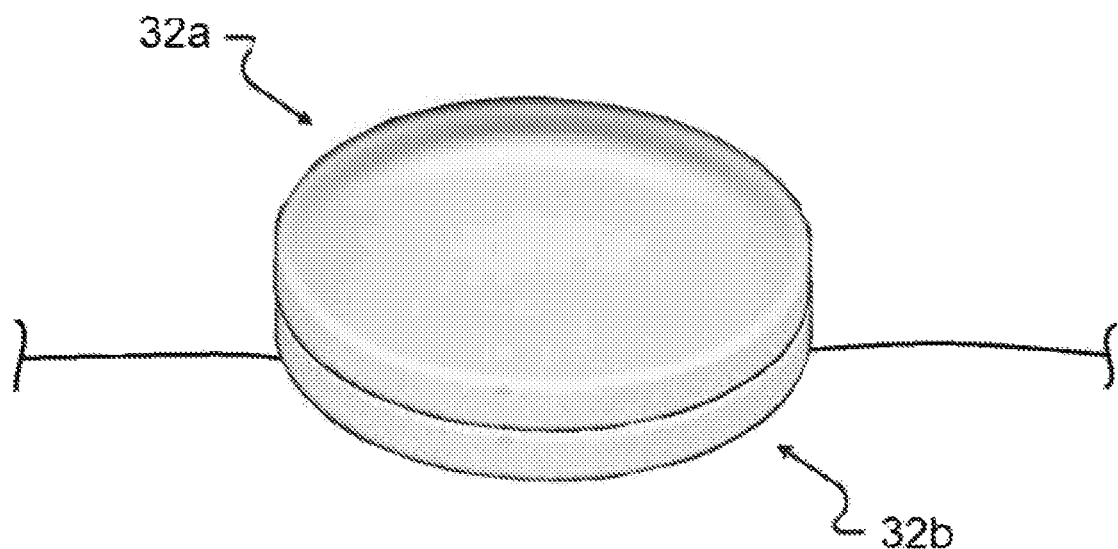
FIG. 4A shows two therapeutic resonant frequency pattern devices stacked on top of each other and placed directly on a patient.

Referring to FIG. 4A, a first device 32a and a second device 32b are provided without a delivery mechanism. In some embodiments, a delivery mechanism may be optionally included depending on a number of factors, including the patient's ailment. The delivery mechanism may activate, modulate, or amplify RFPs among other actions. As described above, the contraction of the muscle alone may provide the excitement necessary to generate frequency responses from the device 32a or carrier layer. The contraction of a muscle may be sufficient when the patient's ailment is a simple muscle strain or other imbalance. However, some patient's ailments prevent the contraction of a muscle or other bodily movement that excites the RFPs imprinted in the device 32a or carrier layer. For example, muscular dystrophy or multiple sclerosis patients may not have a complete range of motion or muscle response to sufficiently excite the device 32a. Therefore, the delivery mechanism provides excitation to the device 32a when there is no other excitation. It will be appreciated that a delivery mechanism may also be used on any patient to enhance or supplemental existing excitation.

The devices 32a, 32b in FIG. 4A are stacked on top of each other and may comprise different materials. The first device 32a may comprise a first composition, and a second device 32b may comprise a second composition. For example, the first device may be imprinted with the RFPs of a muscle formula as discussed elsewhere herein, and the second device may be imprinted with the RFPs of a hypoxic formula. In further embodiments, multiple compositions, devices, carrier layers, or substrates may be combined into a single device 32a.

Mechanical waves include acoustic waves generated by devices such as a piezoelectric transducer and other similar devices. In some embodiments, an acoustic resonator such as a tuning fork may have a frequency range between approximately 62 Hz and 4111 Hz, wherein the tuning fork may excite a resonance frequency in a layer. Other delivery mechanisms may produce ultrasonic waves, which are acoustic waves above the range of normal human hearing. Delivery mechanisms 50 that generate mechanical waves may comprise a frequency generator to control the wave frequency or frequencies, wave form, and wave amplitude among other attributes of the mechanical wave. In a specific example, a FG085 MiniDDS Function Generator is connected to a sheet or membrane with alligator clips or other means of operative connection. The membrane in this embodiment has piezoelectric properties, meaning electric charge accumulates in response to mechanical stress, or vice versa. A particular frequency or frequencies, wave form, and amplitude may be applied to the membrane to alter the properties of the membrane, for example, to match the signal of compounds or bodily components. After an embedding step, the membrane may be used as a substrate or carrier layer or may be added in combination with any layer of the device 32a.

Figure 4B:
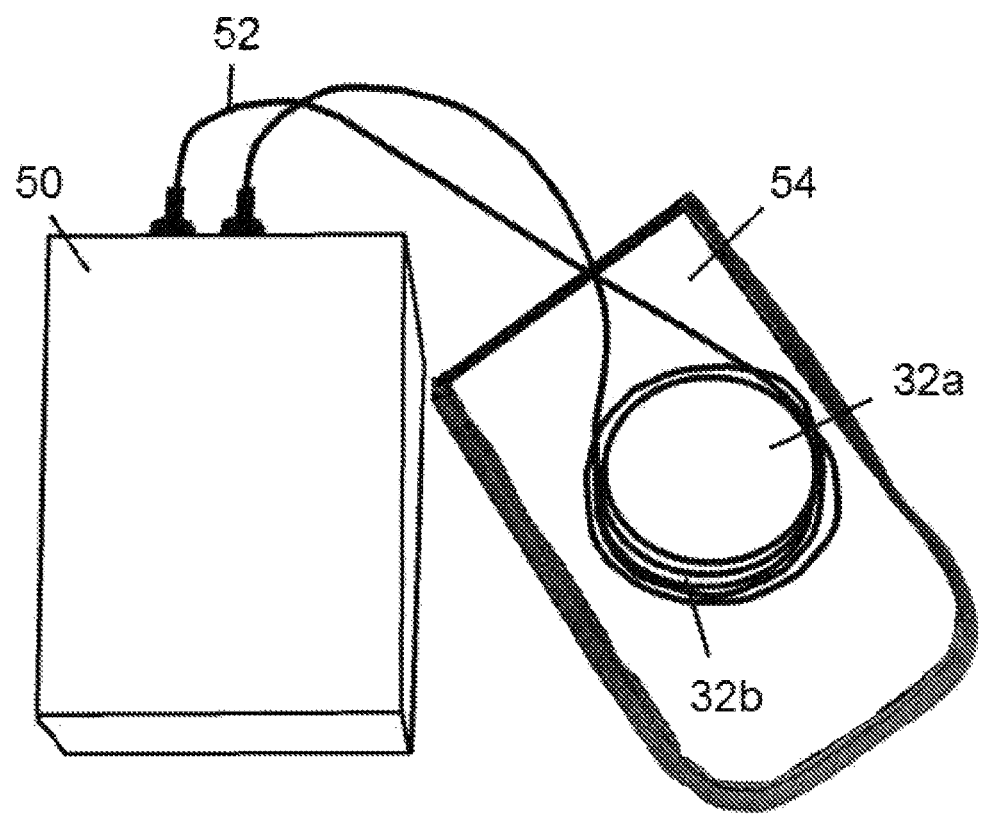
FIG. 4B shows two therapeutic resonant frequency pattern devices and a delivery mechanism having a coil or two electrodes, wherein the two devices and the coil or electrodes are placed in a housing, which is then positioned on a patient.

Referring to FIG. 4B, a first device 32a and a second device 32b are provided with a delivery mechanism 50. In the realm of electromagnetism, the source of an electromagnetic wave may come from a variety of electromagnetic delivery mechanisms 50. For example, frequency generators, Pulsed Electromagnetic Fields ("PEMF"), Transcutaneous Electrical Nerve Stimulation ("TENS"), LASERs, and other similar devices can be used as a delivery mechanism 50 to excite a frequency response in the device 32a. As shown in FIG. 4B, a delivery mechanism 50 may comprise a cable 52 that extends from a main body or housing of the delivery mechanism 50. The cable 52 transmits an electromagnetic wave to the devices 32a, 32b and/or the patient. It will be appreciated that a plurality of cables 52 may be employed, including cables 52 that connect to the delivery mechanism 50 at a single location, not two locations as shown in FIG. 4B. Similarly, a plurality of delivery mechanisms 50 may be employed.

The cable 52 may be positioned in a particular arrangement relative to the devices 32a, 32b. For example, the cable 52 may be arranged in a coil shape around the devices 32a, 32b when the devices 32a, 32b are placed over or in proximity to the tissue to be treated. To preserve this arrangement, the cable 52 and the devices 32a, 32b may be placed into a housing 54 defining a partially enclosed volume such as a pocket. Then the housing 54 is placed over or proximate to a patient's tissue or muscle for therapeutic treatment.

In some embodiments, the delivery mechanism's 50 cable 52 is arranged around the outer perimeter of the one or more devices 32a, 32b to maximize the contact area between the cable 52 and the devices 32a, 32b. In various embodiments, the cable 52 is arranged in a coil having a diameter between approximately ½" and 10". In some embodiments, the cable 52 is arranged in a coil having a diameter between approximately 4" and 7". In one embodiment, the cable 52 is arranged in a coil having a diameter of approximately 5.5". The number of turns the cable 52 makes upon itself may be any number of turns, including one, two, three, four, five, etc. The thickness of the cable 52 in some embodiments may be between approximately 0.5" to 2" thick.

In other embodiments, the cable 52 may be arranged in a coil have a diameter that is less than one or more devices 32a, 32b. In these embodiments, the cable 52 may rest on top of the electrodes, or the cable 52 may be positioned between devices 32a, 32b. In yet other embodiments, the cable 52 is arranged in a coil have a diameter that is greater than the one or more devices 32a, 32b, which creates a space. In some embodiments, this space may be between approximately 0.1" and 2". In various embodiments, this space may be between approximately 0.25" and 1".

Figure 5A:
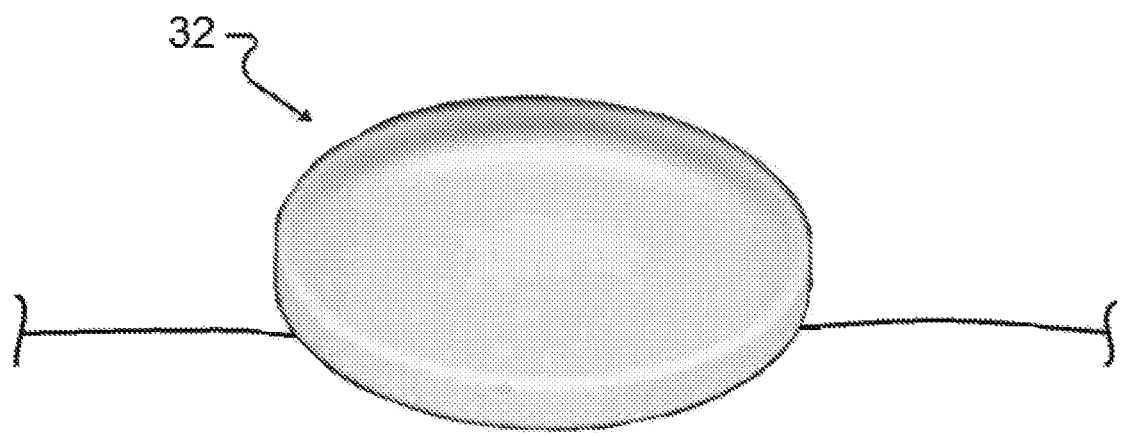
FIG. 5A shows a therapeutic resonant frequency pattern device placed over a muscle or muscle group of a patient.
Figure 5B:
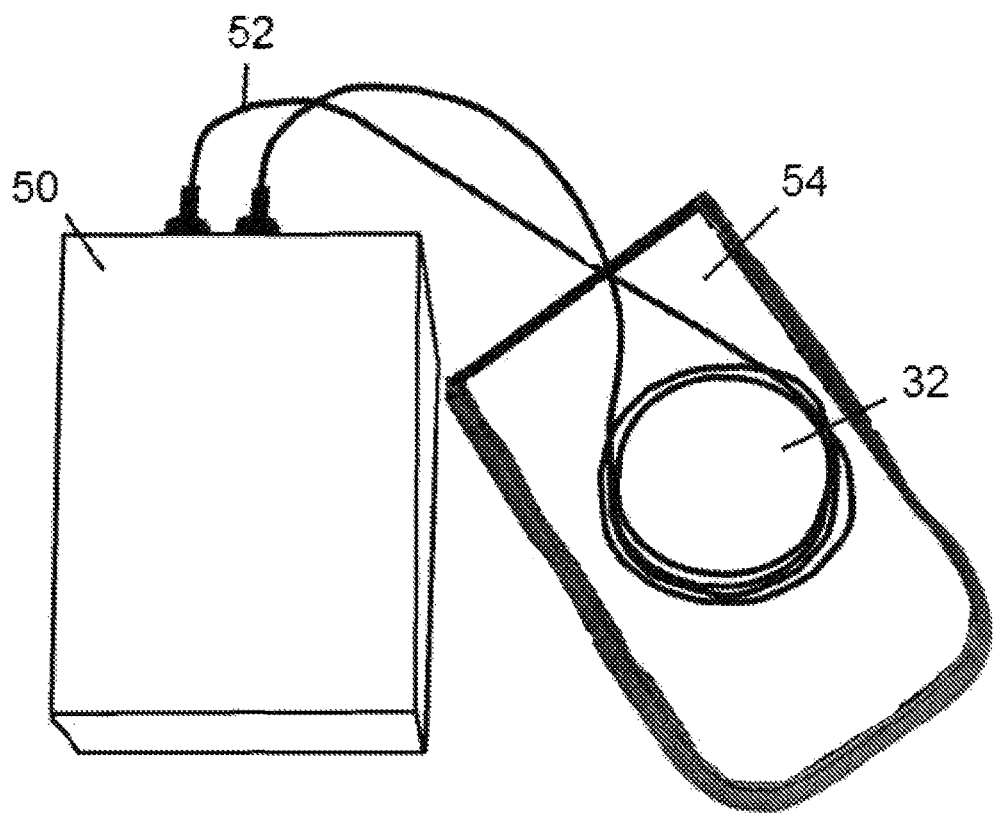
FIG. 5B shows a therapeutic resonant frequency pattern device and a delivery mechanism having a coil or two electrodes, wherein the device and the coil or electrodes are placed in a housing, which is then positioned over a muscle or muscle group of a patient.

Referring to FIGS. 5A and 5B, a single device 32 may be utilized with or without a delivery mechanism 50 as described in FIGS. 4A and 4B, respectively. As described elsewhere herein, a single device 32 may be imprinted with therapeutic RFPs associated with a single formula such as a hypoxic formula. In other embodiments, the device 32 may be imprinted with more than one therapeutic RFPs associated with more than one formula. In some embodiments, the device 32 is imprinted with therapeutic RFPs associated with both a hypoxic formula and another formula. These multiple therapeutic RFPs may be imprinted serially or simultaneously. PEMF devices emit pulsations of electromagnetic radiation. The pulse wave or rectangular wave form is the preferred wave form associated with PEMF delivery mechanisms. However, PEMF delivery mechanisms may also utilize sine waves, square waves, triangle waves, saw-tooth waves, and any other waveform commonly known in the art, or waveforms of arbitrary shape constructed to efficiently convey therapeutic RFPs to affected tissue. Other important parameters associated with the PEMF delivery mechanism include the frequency or frequencies of the electromagnetic radiation and the amplitude of the electromagnetic radiation, wherein the parameters are independently adjustable. PEMF delivery mechanisms used in combination with devices 32 described elsewhere herein can be used to treat pain, including chronic pain. Further literature regarding the benefits of PEMF treatment may be found in Rheumatol Int (2010) 30:571-586; Alternative Therapies, July/August (2003), Vol. 9 No. 4, 38-48; and Cell Biochem Biophys (2013) 67:1229-1237, which are incorporated herein in their entirety by reference.

For the PEMF delivery mechanism and other delivery mechanisms that utilize electromagnetic radiation, a variety of frequencies may be utilized. For example, radio waves (3 Hz-300 MHz), microwaves (300 MHz-300 GHz), infrared light or waves (300 GHz-400 THz), visible light (400 THz-770 THz), ultraviolet light (770 THz-30 PHz), X-rays (30 PHz-30 EHz), gamma rays (more than 30 EHz), and low-frequency waves (below 3 kHz) are all frequencies that the electromagnetic delivery mechanisms may utilize. Typically, lower frequencies are preferred in the utilization of PEMF devices as a delivery mechanism. In some embodiments, the PEMF delivery mechanism produces a frequency or frequencies less than approximately 3,000 Hz. In further embodiments, the PEMF delivery mechanism produces a frequency or frequencies less than approximately 100 Hz. In yet further embodiments, the PEMF delivery mechanism produces a frequency or frequencies less than approximately 24 Hz.

In one embodiment, a device may be imprinted with frequencies that correspond with the natural resonance of oxygen molecules or other oxygen substances, which typically ranges between 57 and 64 GHz. Further, the device may be excited with these frequencies. An oxygen-specific device may be used alone or in combination with other devices described elsewhere herein.

Further, a frequency sweeping option may be utilized with electromagnetic delivery mechanisms. In one embodiment, the frequency sweep occurs between a first and a second reference frequency over a period of time. In some embodiments, the reference frequencies are approximately 0.5 Hz and 32 kHz. Reference frequencies may also include Schumann resonances (7.83 Hz and harmonics thereof, including 14.3, 20.8, 27.3, and 33.8 Hz). Further, reference frequencies can include any frequency of the electromagnetic spectrum. The frequency sweep occurs over time, but the sweep is not necessarily a continuous sweep between two reference frequencies. For example, a delivery mechanism may emit a first reference frequency for a first time period, and second reference frequency for a second time period, a third reference frequency for a third time period, and so on. One skilled in the art will appreciate various combinations of references frequencies and time periods to implement a frequency sweep option for a delivery mechanism.

One particular example of a PEMF is a device which pulses current to produce a pulsed electric field. This is significant because the coil applicator can be turned to provide predominately positive or predominately negative fields to the body. Using approximately 160 volts, it is possible to pulse electromagnetic waves with a frequency or frequencies less than 20 kHz and a lower magnetic strength limit of 10,000 gauss. In some embodiments, the voltages for the PEMF device may range between approximately 120 to 240 Volts. In various embodiments, the electromagnetic waves may be as low as 100 MHz. Further, in certain embodiments, the magnetic strength of the PEMF device may be between approximately 1 to 30,000 gauss. Further yet, in some embodiments, the magnetic strength of the PEMF devices may be between approximately 2,400 to 21,000 gauss.

PEMF delivery mechanisms and other delivery mechanisms may be used with one or more devices according to treatment protocols discussed elsewhere herein. For example, referring to the protocol discussed in FIG. 6, if there is an observed, isometric contracting or "unlocking", then at block 64, the device is placed on the muscle or group of muscles, or in other embodiments, the device is placed over or in proximity to the particular tissue or muscle along with a delivery mechanism. The various parameters of the PEMF delivery mechanism may be adjusted for a particular patient and/or a particular ailment. For example, autoimmune issues may require lower amplitude and higher frequency electromagnetic waves while neurological issues may require higher amplitude and lower frequency electromagnetic waves. Then, the protocol proceeds like the protocol in FIG. 6 and then at step 72 the device and delivery mechanism are removed from the patient.

Next, TENS delivery mechanisms utilize an electric current for nerve stimulation. TENS devices may modulate the pulse width, frequencies, amplitude, wave form, etc. of electromagnetic waves. Generally, TENS is applied at high frequency (>50 Hz) with an intensity below motor contraction (sensory intensity) or low frequency (<10 Hz) with an intensity that produces motor contraction. Typically, the TENS devices includes one or more electrodes to deliver the electromagnetic wave. Dermal patches may be incorporated to adhere the electrode to a portion of a user's skin such that electrode is fixed relative to a muscle or muscle group. One skilled in the art will appreciate that a patch or other similar device may be used with other delivery mechanisms such as the PEMF device to secure the delivery mechanism relative to the muscle or muscle group.

In one particular example of the present invention, the carrier layer is a quartz crystal with a particular size and cut. A quartz crystal has piezoelectric properties wherein an electric field distorts the physical shape of the quartz crystal. When the electric field is altered the quartz crystal changes shape and generates an electric field of its own. The rate of expansion and contraction of the quartz crystal can be the resonance frequency or resonance frequencies of the carrier layer. In other embodiments, fused silica, which is a non-crystalline form of silicon dioxide, may be used in combination with quartz or substituted in place of quartz.

In some embodiments of the present invention, the portion of the device 32 that comprises a resonance frequency may be heated or cooled to affect the performance of the layer. In one embodiment, the carrier layer comprises a resonance frequency. The carrier layer may be heated or cooled when the carrier is placed in proximity to the muscle or muscle group, and the delivery mechanism is placed in proximity to the carrier layer. Depending on attributes of the carrier layer such as the cut, the change in temperature can affect the frequencies generated by the excitation of the carrier layer, and the change in temperature can directly enhance the therapeutic on the user.

Figure 6:
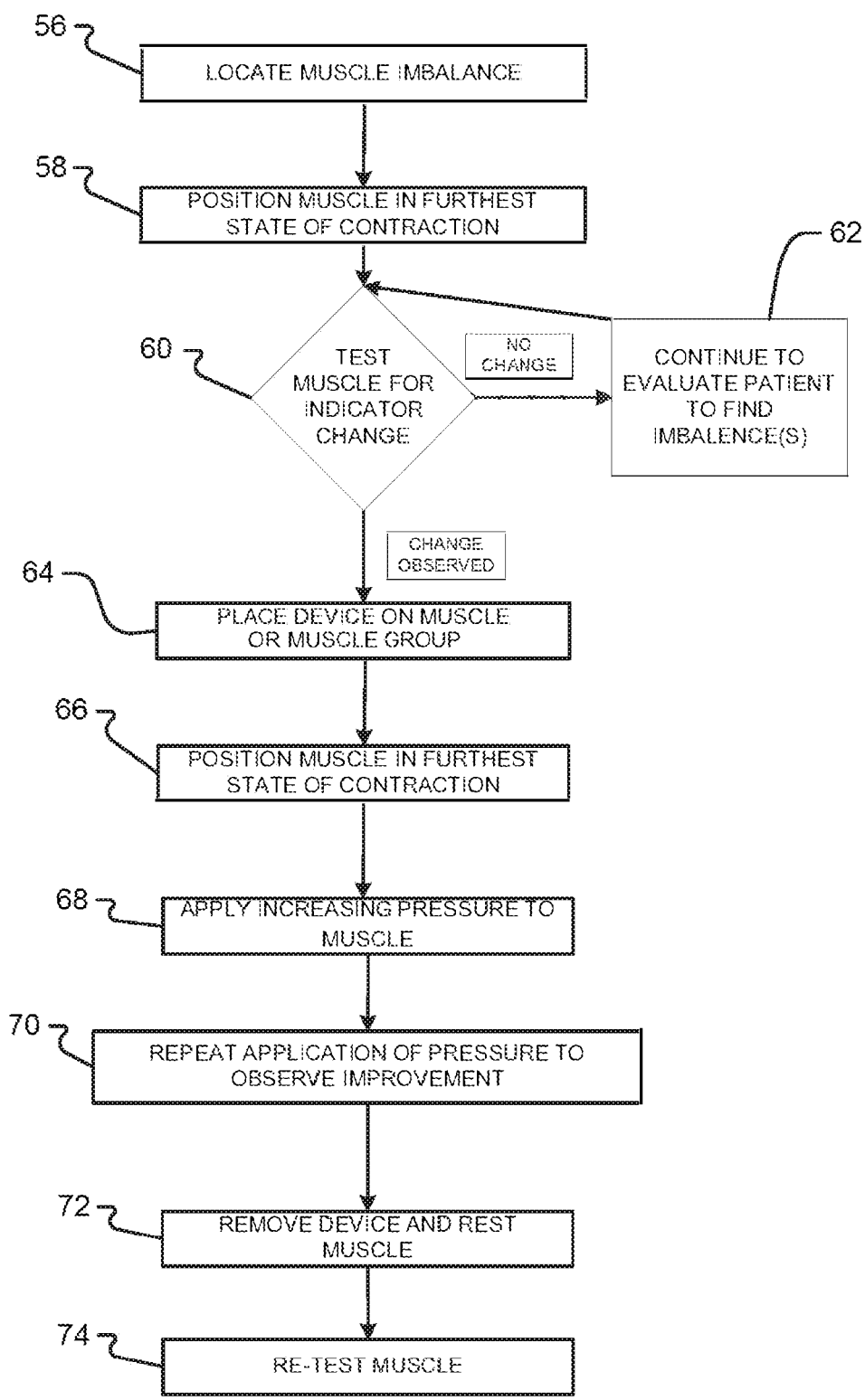
FIG. 6 is a simplified flow diagram of the method of using or applying the device of the present invention.

Referring to FIG. 6, a simplified flow diagram is provided for explanation of one preferred embodiment of the method of the invention. Al block 56, as a first step, a caregiver locates a muscle imbalance. At block 58, the affected body part is positioned so that the targeted muscle is in the furthest state of contraction. This contracted position is held for approximately 5 seconds. At block 60, the muscle is tested for an indicator change by applying a steady, consistent pressure. If there is no indicator change, that is, if there is no observed, eccentric contraction, "unlocking", or failure of the muscle, then at block 62, the patient continues to be checked/evaluated for other muscle imbalances. If there is an observed, eccentric contraction or "unlocking", then at block 64, the device 32 is placed on the muscle or group of muscles, or in other embodiments, the device 32 is placed over or in proximity to the particular tissue, muscle, or muscle group. At block 66, the targeted/imbalanced muscle is again placed in its furthest state of contraction. At step 68, increasing pressure is applied for approximately 5 seconds to activate the muscle fibers, and the associated spindle cells, golgi tendon organs and golgi ligament organs. This activity of block 68 is repeated a number of times, shown at block 70. During this repeated application of pressure over 5 second time periods, the caregiver should observe improved muscle function. In clinical trials, it has been shown that repeating this activity three or four times has been adequate to resolve many muscle imbalance problems. At step 72, the device 32 is removed from the patient, and the muscle is allowed to rest for a period of time, preferably for about 2 minutes. At step 74, the muscle is retested by placing the muscle back to its furthest state of contraction. If the procedure has been successful, the targeted muscle(s) should now isometrically contract lock strongly against monitoring pressure.

The method described in reference to FIG. 6 prescribes placement of the device 32 on the muscle or group of muscles; however, it should be understood that the device 32 can be placed upon other body parts, to specifically include those muscles and muscle groups that have been found to have an imbalance. Additionally, although the method described prescribes application of repeated and progressively increasing pressure over 5 second time periods, other methods of the present invention may include other protocols for application of pressure over other time periods, as well as the number of cycles in which pressure is applied. For example, for some muscle groups, it may be found that applying pressure over lesser or greater time periods may be preferred. As best understood, the resonance frequencies are transmitted to the patient passively. For instance, the movement of the individual muscle or muscle group excites a frequency response from the device 32. In other embodiments, a delivery mechanism may be used to actively excite a frequency response from the device 32.

In an alternative embodiment, the patient has a more active role in the steps at blocks 56, 58, 60 wherein the user performs a predetermined motion. Then, depending on the effort required to perform the predetermined motion, a muscle or tissue imbalance may be located. The device and other components described herein may be placed over the particular muscle or tissue imbalance for a predetermined time. In some embodiments, the predetermined time is between approximately 2 to 10 minutes. Next, the patient may re-perform the predetermined motion for the steps at blocks 66, 68, 70 to observe if more treatment is required. In various embodiments, multiple devices and associated components may be deployed on a patient to achieve the desired effect.

Data has been collected in a proof-of-concept study and an MB-approved university trial assessing muscle function using the device and method of the invention. In initial clinical studies the invention has been shown to reliably produce consistent improvements in muscle function. One common measure of muscle function is termed Electromyography or EMG that measures the electrical activity of the individual motor units as they shorten during contraction. In EMG, the Electromyograph is attached to a recording electrode which is either a needle inserted into the muscle to record muscle activity, or to a transcutaneous electrode that records electrical activity of the muscle from the surface of the skin. In the university study, transcutaneous electrodes were used. When the muscle is attached to either needle or transcutaneous electrodes, muscle activity is measured by electrical frequencies sent to the Electromyograph, which can then convert these raw frequencies into several types of electromyograms (EMGs). One common type of electromyogram is called an Integrated Power Spectrum. This graphically presents the number of motor units actively contracting in the muscle over time and is measured in millivolts. The greater the number of motor units contracting at any one time indicates a stronger muscle contraction.

Additional embodiments of the invention are provided in FIGS. 7A-7C that catalyze a response of a patient to a therapy. Referring to FIG. 7A, a device 76 may be imprinted with key frequencies of the resonant frequency pattern of the formula sample, and the device 76 may be imprinted with the key frequencies using, as described herein, a plasma generator system, a PEMF device, etc. During operation, the imprinted device 76 is placed proximate to or on a patient 80. Then, a therapy 78 is applied to the patient, and the therapy 78 may be an electromagnetic therapy or a non-electromagnetic therapy. One example of an electromagnetic therapy is a PEMF device delivering a pulsed electromagnetic frequency to the patient. The imprinted device and the key frequencies imprinted in the device catalyze the response of the patient to the electromagnetic therapy. Examples of non-electromagnetic therapies include, but are not limited to, a pharmaceutical compound, a physical and chiropractic therapy, a homeopathy therapy, an acupuncture therapy, psychological counseling, Qigong medicine, and Ayurvedic medicine. Again, the imprinted device and the key frequencies imprinted in the device catalyze the response of the patient to the non-electromagnetic therapy.

FIG. 7B shows another embodiment of the invention that combines or mixes frequencies from multiple sources. Key frequencies 82 of a resonant frequency pattern of a formula sample are generated by an arbitrary waveform generator 83, and a PEMF device produces pulsed electromagnetic frequencies 84. A nonlinear element 86 such as a diode combines these electronic signals 82, 84 into a mixed electronic signal. Specifically, nonlinear element 86 can combine the key frequencies 82 and the sum and difference frequencies of the key frequencies 82 with the pulsed electromagnetic field frequency 84. An amplifier may increase the amplitude of the mixed electronic signal before the mixed electronic signal is sent to a transmitter 88 such as a coil or an antenna. The mixed electronic signal is transmitted to the patient 80, and the additional of the key frequencies 82 to the pulsed frequency 84 catalyzes a response of the patient to the pulsed frequency 84.

FIG. 7C illustrates an embodiment of the invention where key frequencies 82 are replicated by the arbitrary waveform generator 83 then delivered by a transmitter 88 to a patient 80 to catalyze a response of the patient 80 to a therapy 78. Like the embodiment described with respect to FIG. 7A, the therapy 78 may be an electromagnetic therapy or a non-electromagnetic therapy. One example of an electromagnetic therapy is a PEMF device delivering a pulsed electromagnetic frequency to the patient. The key frequencies 82 catalyze the response of the patient to the electromagnetic therapy. Examples of non-electromagnetic therapies include, but are not limited to, a pharmaceutical compound, a physical and chiropractic therapy, a homeopathy therapy, an acupuncture therapy, psychological counseling, Qigong medicine, and Ayurvedic medicine. Again, the key frequencies 82 catalyze the response of the patient to the non-electromagnetic therapy.

Figure 8:
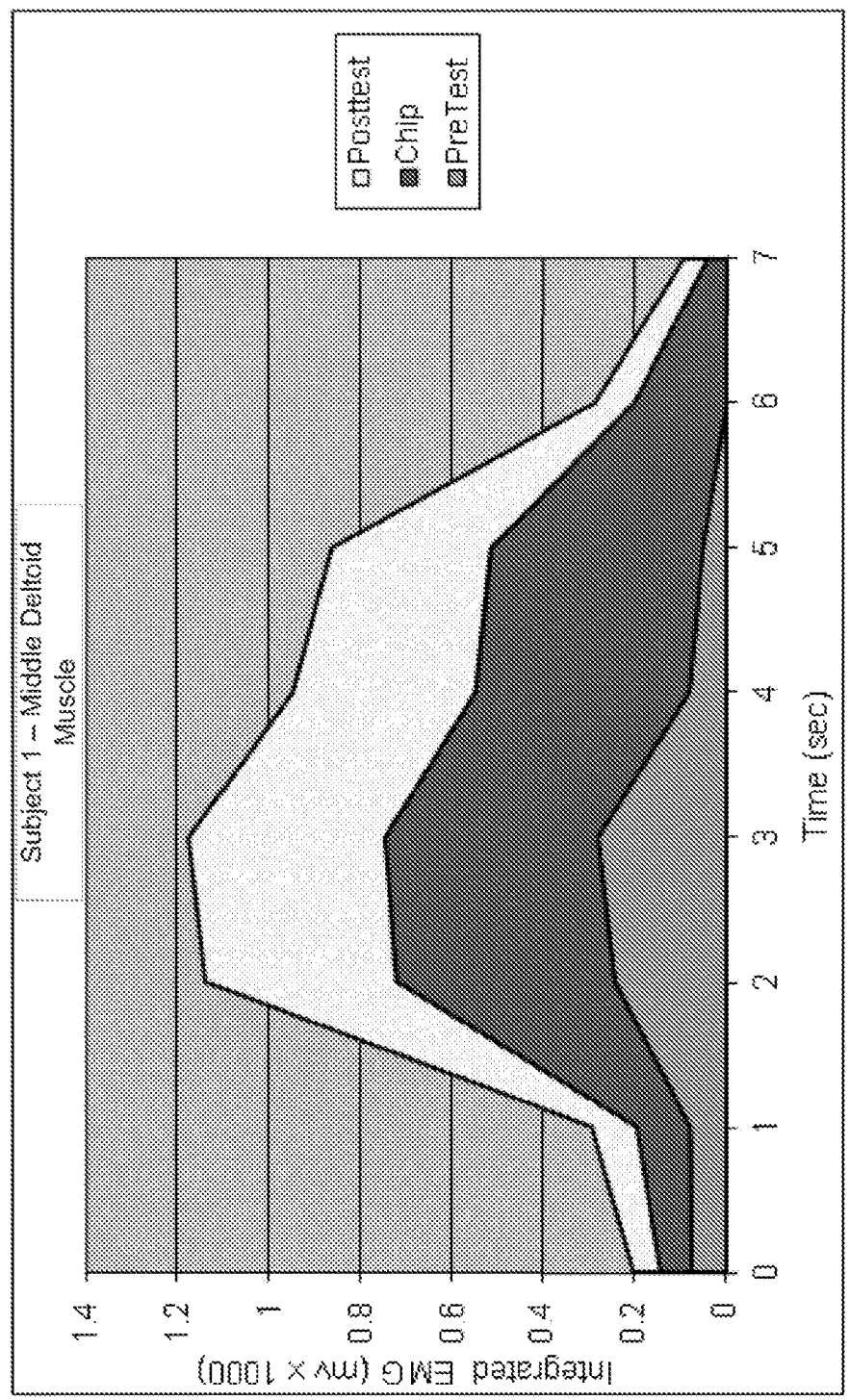
FIG. 8 is a graphical representation of data obtained during proof-of-concept testing showing improvements in muscle function.
Figure 9:
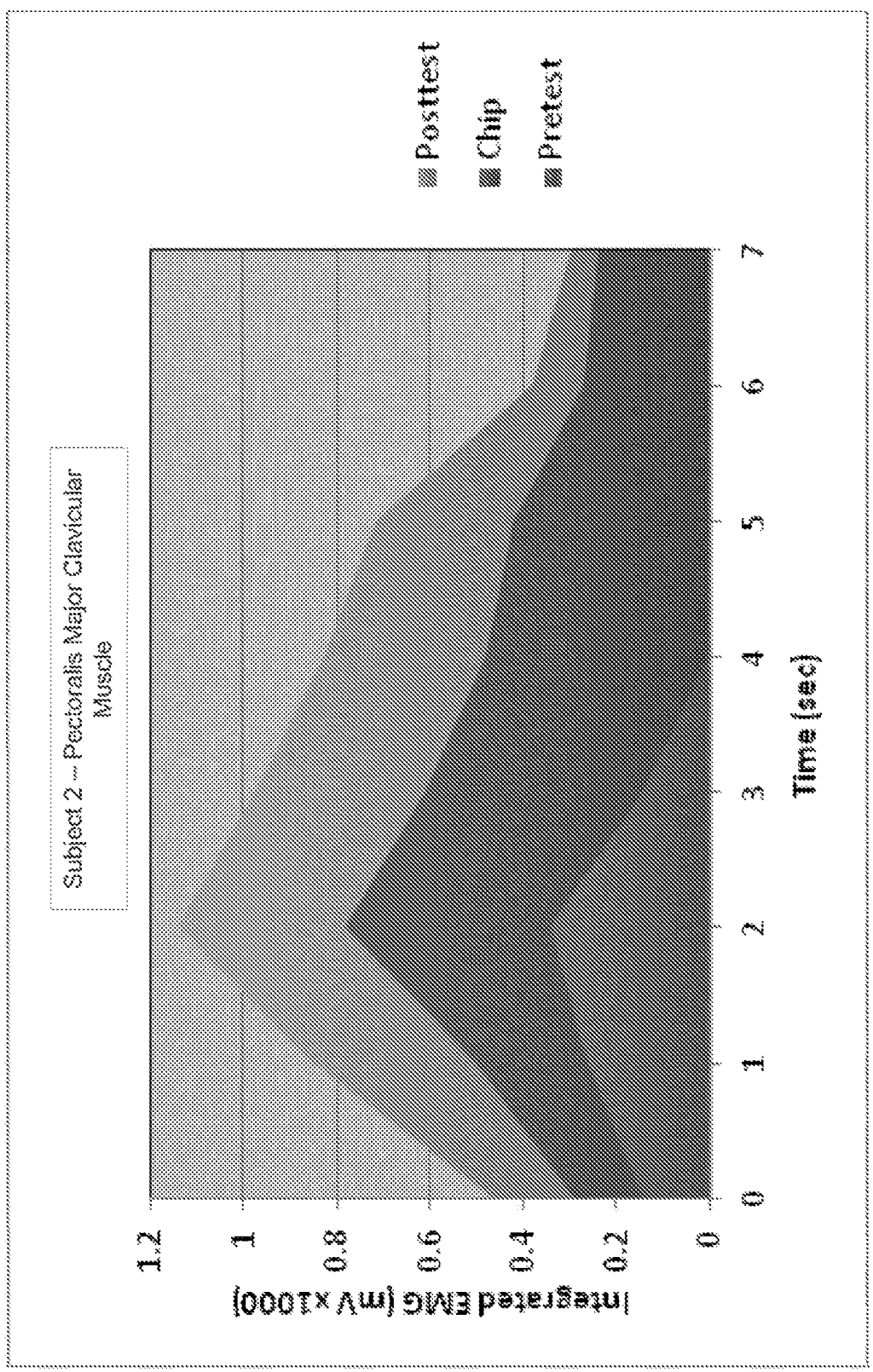
FIG. 9 is another graphical representation of data obtained during proof-of-concept testing showing improvements in muscle function.

FIGS. 8 and 9 are graphical examples of muscle testing for two different muscles conducted in preliminary human pilot studies. In these examples, the subject's muscles became eccentrically contracted or "unlocked" when manually tested, and the muscles could only facilitate a small number of motor units when tested; accordingly, the muscles failed under only moderate pressure applied to the corresponding limbs of the muscles. In both examples the muscles were under-facilitated because not enough motor units could fire to fully facilitate the muscle and isometrically contract or "lock". As shown, the muscles tested were a middle deltoid muscle (FIG. 8) and a pectoralis major clavicular muscle (FIG. 9), The PreTest data (the PreTest referenced in the legends of the graphs of FIGS. 8 and 9) reflects the states of the muscles when initially evaluated.

In one test, the device 32 is applied to a muscle or group of muscles, and the arm moved into the test position, where its fibers were aligned and shortened to provide maximal mechanical advantage during the test. With both muscles there was a dramatic increase in the number of motor units recruited (activated) by the pressure applied to the arm to isometrically contract or "lock" the muscle and hold it in place throughout the 5 to 6-second duration of the muscle test while the device 32 was applied to the muscle or group of muscles. As shown in the test data, there was a rapid increase in the EMG power spectrum of both muscles as pressure was applied, then sustained full 5 to 6 seconds pressure was applied, and then the rapid return to baseline once the pressure had ceased.

The device 32 was removed from the muscle or group of muscles, and after a 3 to 5 minute rest period, the muscle was tested once again, (this later test referenced as the Posttest in the legends of the graphs). As shown, both muscles recruited even a larger number of motor units than when the device 32 was being applied to muscle or group of muscles. The Posttest data indicates that the muscles developed a full isometric contraction or "lock" signifying a "reset" of the proprioceptors that had been inhibiting these muscles before the treatment.

Figure 10:
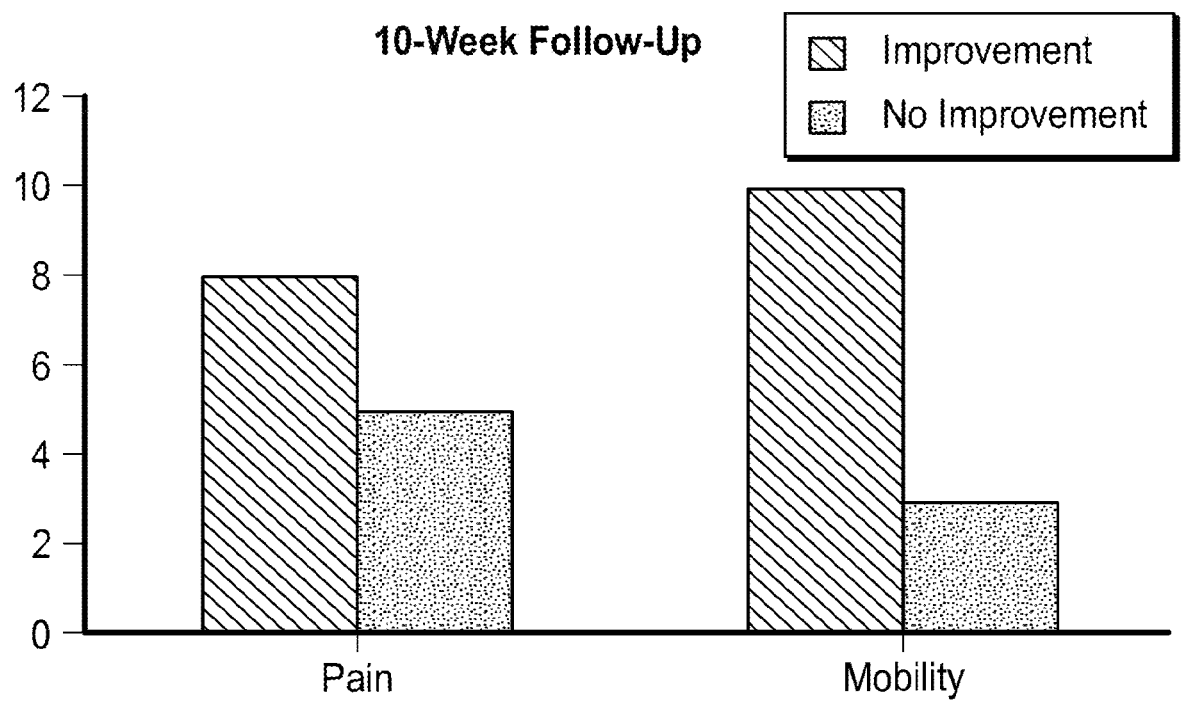
FIG. 10 is another graphical representation of data obtained during proof-of-concept testing showing improvements in pain and mobility after an extended period of time.

Referring to FIG. 10, this figure indicates that the effects from application of the device 32 in a treatment appear to be long-lasting. In this Figure, the y-axis represents a range of mobility and a pain scale in which 0 represents a state in which there is no mobility or no pain, and 10 represents a state in which there is full mobility or maximum pain. This figure reflects data obtained in a proof of concept study of a group of thirteen individuals with chronic shoulder pain and muscle dysfunction who were treated only one time, yet this study group showed a greater than 77% increase in limb mobility (measured as a function of a mobility scale from 1-10). The study group also showed a nearly 62% reduction in pain ten weeks after treatment (measured as a function of a pain scale from 1-10). As indicated in the graph of FIG. 10, dark bars (left) represent patients that showed improvement for pain and mobility, while the lighter bars (right) represent those patients that did not show measurable or appreciable improvement. The graph of FIG. 10 clearly shows that patients did show improvement, particularly in mobility.

In summary, the device and method of the present invention are capable of producing rapid improvement in muscle dysfunction. The therapeutic benefits can be realized by evaluating a starting point in which a muscle is in a state of overt imbalance, and is transferred to a new state of homeostasis in less than five minutes. Many of these rapid corrections were evaluated as long-lasting.

The invention now being generally described will be more readily understood by reference to the following example, which is included merely for the purposes of illustration of certain aspects of the embodiments of the present invention. The example is not intended to limit the invention, as one of skill in the art would recognize from the above teachings and the following examples that other techniques and methods can satisfy the claims and can be employed without departing from the scope of the claimed invention.

EXAMPLES

This example provides an IRB-approved university study demonstrating the effect of a muscle optimization (MO) device of the present invention on the ability of the muscle to produce force and surface muscle energy activity. The muscle optimization device is postulated to improve muscle function by resetting muscle proprioception and improving muscle strength. Preliminary pilot studies using surface electromyography (EMG), described above, provided sufficient positive results to warrant a full-protocol study with human subjects using both EMG and a force gauge meter to test consistency and correlation.

The study is a Test-Retest design wherein the initial state of muscle imbalance was assessed with quantitative surface EMG. The muscle optimization device was applied over light clothing on the muscle or group of muscles. The muscle with identified weakness was then activated, and force applied during testing the muscle was determined by a multi-directional force transducer, and the muscle response quantified using surface EMG. The results were analyzed for correlation between the objective force applied and the number of motor units recruited during each test. The major outcome measures are peak force generated and surface EMG curve produced during isometric or eccentric muscle contractions.

Study subjects were selected from healthy, active athletes participating in a variety of sports such as volleyball, tennis, racquetball, basketball, soccer, ice hockey, rock climbing, boxing, football, lacrosse or Nordic skiing. Participants were selected based on self-reports as being physically healthy, but who experienced muscle weakness in certain muscles/muscle groups, such as muscle imbalances of the shoulder joint: supraspinatus; middle deltoid; anterior deltoid; pectoralis major; clavicular division or latissimus dorsi. Study subjects were between the ages of 18 to 35, reportedly in good health, with no acute shoulder injury, inflammation or pain. Those subjects who reported a degenerative muscle condition or neurologic disease, such as multiple sclerosis, or asthma, were excluded from the study.

Inclusion Criteria for the test subjects: To address the inherent variability of muscle function, the study was limited to volunteer subjects who have an imbalance or weakness in one or more of the following, easily isolatable muscles of the shoulder joint.
 supraspinatus
 middle deltoid
 anterior deltoid
 pectoralis major, clavicular division
 latissimus dorsi These muscles have been selected upon the basis of being accessible to attach the surface EMG electrodes, and agonists that can be isolated with respect to muscle fiber alignment and have limited synergist activity until relatively higher force has been applied. These are also all muscles for which multiple-examiner reliability is high. Age: between the ages of 18 to 35

Sex: male or female Health Status: self-reported in good health, Sport: subjects will be active in a sport or training that may lead to over use or misuse of shoulder muscles, specifically: volleyball, tennis, racquetball, basketball, soccer, ice hockey, rock climbing, Nordic skiing, martial arts, crew.

Exclusion Criteria for the test subjects: Chronic illness or injury: Self-reported chronic shoulder problems; A degenerative muscle or neurologic disease such as Multiple Sclerosis or asthma: Previous injuries, including acute shoulder injury, including inflammation or pain: Neck, whiplash, or spinal column injury(s); Past Surgeries: A subject having undergone any past surgeries on arm; shoulder or neck.

Subjects participating in the study underwent muscle testing to identify inhibited/weak selected upper body muscles. Identification of muscle inhibition or weakness was assessed by placing the subject's arm in the test position and then asking the subject to "hold" against a pressure applied by the experimenter via the held-hand force transducer. The outcome of the test was scored on a qualitative +3 Scale and assigned a score of 1, 2 or 3. The direction of the pressure applied by the experimenter (e.g. "hold" your arm up with the thumb turned downward, or "hold" your arm into your side, etc., will varied depending upon which muscle was being tested. Those subjects scoring a "3" on the muscle test were assigned to the control group, subjects scoring a "1" or a "2" were assigned to the experimental group. Surface EMG electrodes were placed on the surface of the skin over the inhibited/weak muscle (for the experimental group subject), and over a standard muscle for the control group, using standard electrode placement procedures. Replicate tests were carried out on each muscle selected for assessment in the following sequence:

Control Test: Assessment of the initial muscle imbalance for 6 seconds (3 trials);

MO Device Test: Assessment of the muscle response with the MO Device placed on clothing above the muscle or group of muscles and the muscle activated for 6 seconds (3 trials);

3) The Post-MO Device Test: Assessment of the muscle response following MO Chip therapy with no Chip on the body for 6 seconds (3 trials).

The amount of pressure was recorded using a hand-held force transducer applied by the experimenter and the EMG signal was recorded from the surface electrodes. Testing time for each subject is estimated to be no longer then one hour.

Testing Protocol and preparation of selected muscles for Surface Electromyography (EMG): Muscles that have met the inclusion criteria (either a weak muscle or a control muscle) were prepared for surface EMG recording and attached to the EMG to insure a good signal to noise ratio. The BioNomadix™ wireless EMG system (BioPac Inc.) is used to collect the muscle activity data. First, the skin is cleaned using an alcohol pad and the electrodes (EL500, BioPac Inc) are affixed to the surface of the skin above the belly of the muscle of interest. The ground electrode is affixed to an area without muscle activity.

The force transducer (microFET2) is turned on using the on/off switch, and sensitivity setting set too high. The data recording software, ErgoPak, is launched on the PC, and the meter linked via the blue tooth dongle with the software.

Muscle Test Position: The muscle(s) selected for monitoring are placed in their prescribed muscle testing position to reduce synergist(s) recruitment and to isolate the chosen muscle as much as possible as the Prime Mover or PM for that specific action. The arm is placed into the specific test position in maximal concentric contraction to align the muscle fibers of the Prime Mover, and reduce recruitment of its synergist(s). The subject is asked to "hold" their arm in this position and informed by the monitor exactly how and in which direction pressure will be applied. The subject is then asked to "hold" as the monitor begins to slowly apply increasing pressure in the test direction over approximately 2 seconds, and if the muscle isometrically contracts or "locks" to maintain that pressure for 2 seconds, then slowly release the pressure applied over approximately 2 seconds. The pressure applied is an appropriate force for the muscle tested. With this appropriate force, a clear isometric contraction or "Lock", or eccentric contraction or "Unlock" is observed, and the results recorded. The test is repeated three times to obtain mean values for each muscle tested.

Muscle Optimization Device (MO) Procedure: Muscles that eccentrically contract or "unlocked" in the screening testing, and the control muscle were re-tested after a Muscle Optimization Chip was placed on top of clothing above subject's muscle or group of muscles, and the triplicate testing repeated, as described above. Force-time record, surface EMG time record and peak force were recorded. Rating of muscle function (1, 2 or 3) by tester was recorded.

Muscle Optimization Device (MO) Re-Test Procedure: The MO was taken off and the muscle was re-tested in the triplicate testing procedure described above. Three to five minutes were given between the initial testing and the subsequent MO trials. Electrodes only remained affixed to the surface of a subject's skin for less than or equal to one hour in time.

A within-subject ANOVA was used to determine significant differences between conditions in terms of the maximum pressure exerted, the trial-to-trial variation in the pressure exerted, the mean peak EMG signal, and the root mean square of the EMG signal. The surface EMG results were presented graphically for each test condition, without the MO Device and with the MO Device on the muscle or group of muscles.

Figure 11:
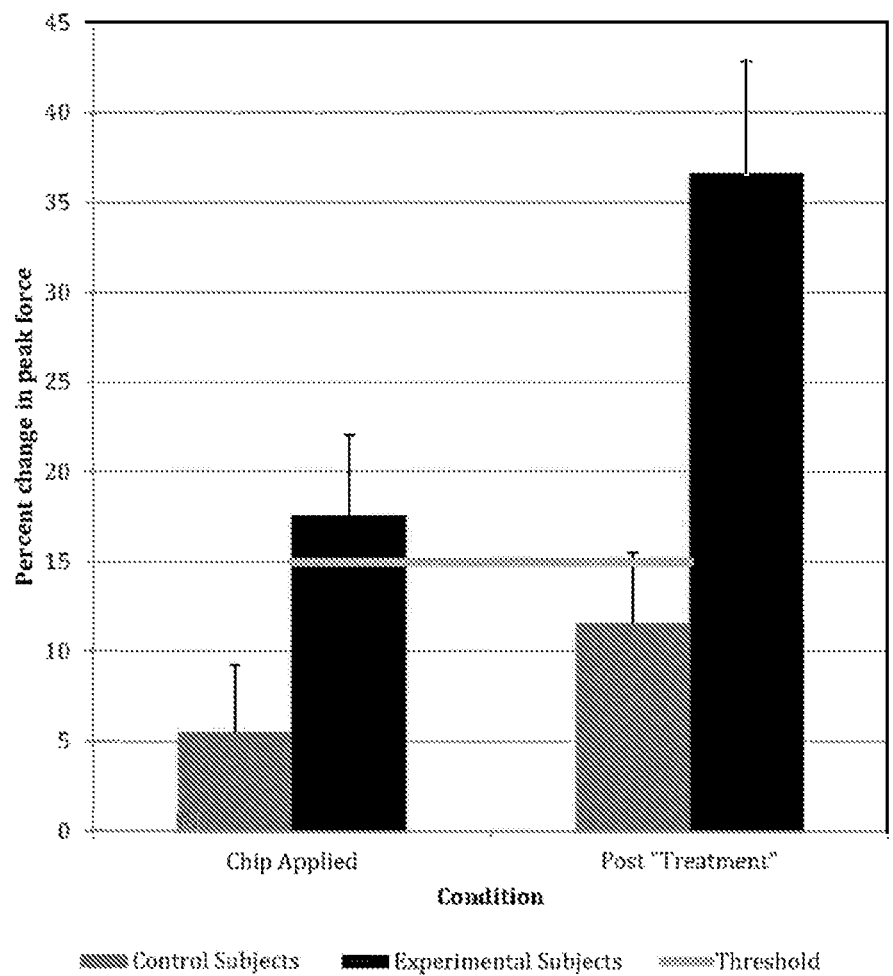
FIG. 11 shows the percentage change in peak force observed between the test conditions, results from the interim analysis of the Pilot Study described in the Examples section of this disclosure. A significant difference was observed in change in peak force between experimental and control subjects, p<0.05. Additionally, the Threshold represents a meaningful change in force, based upon published literature.
Figure 12:
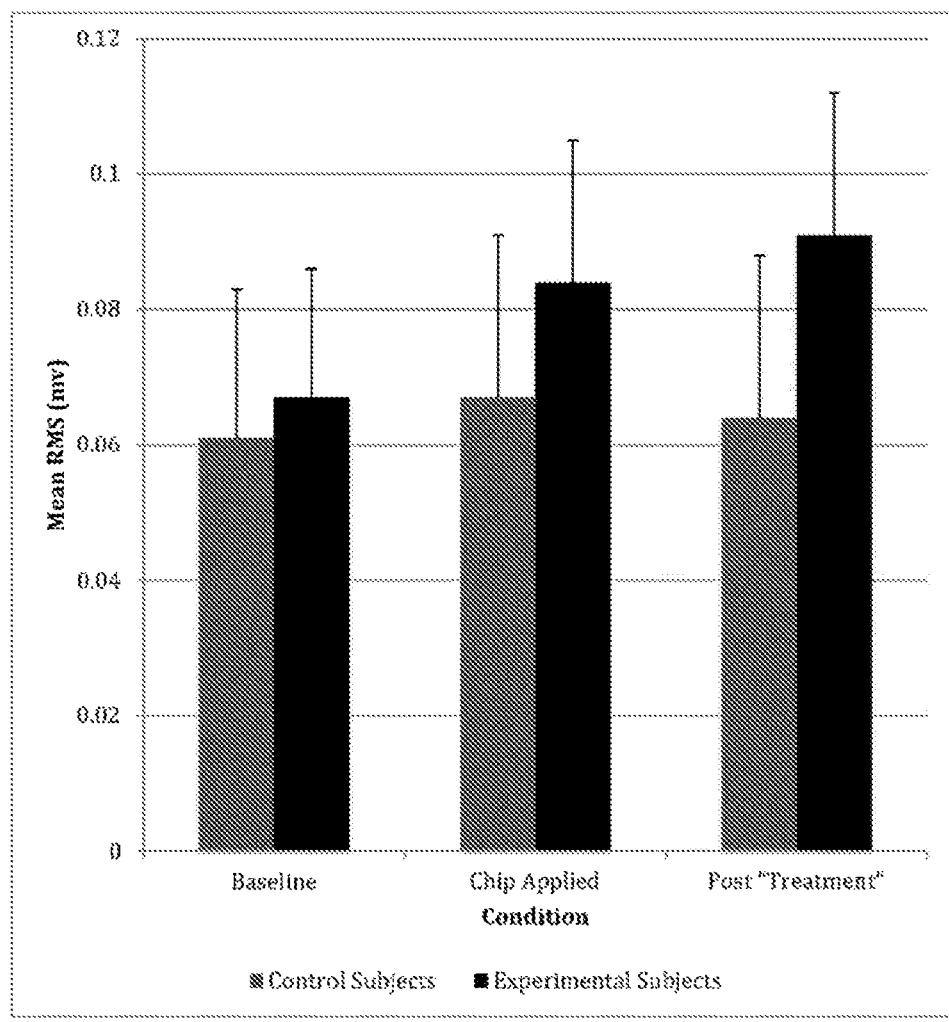
FIG. 12 shows the mean EMG Root Mean Square for the three test conditions, results from the interim analysis of the Pilot Study described in the Examples section of this disclosure. A significant difference was observed between Chip Applied and Post "Treatment" for Experimental Subjects, p<0.05.
Figure 13:
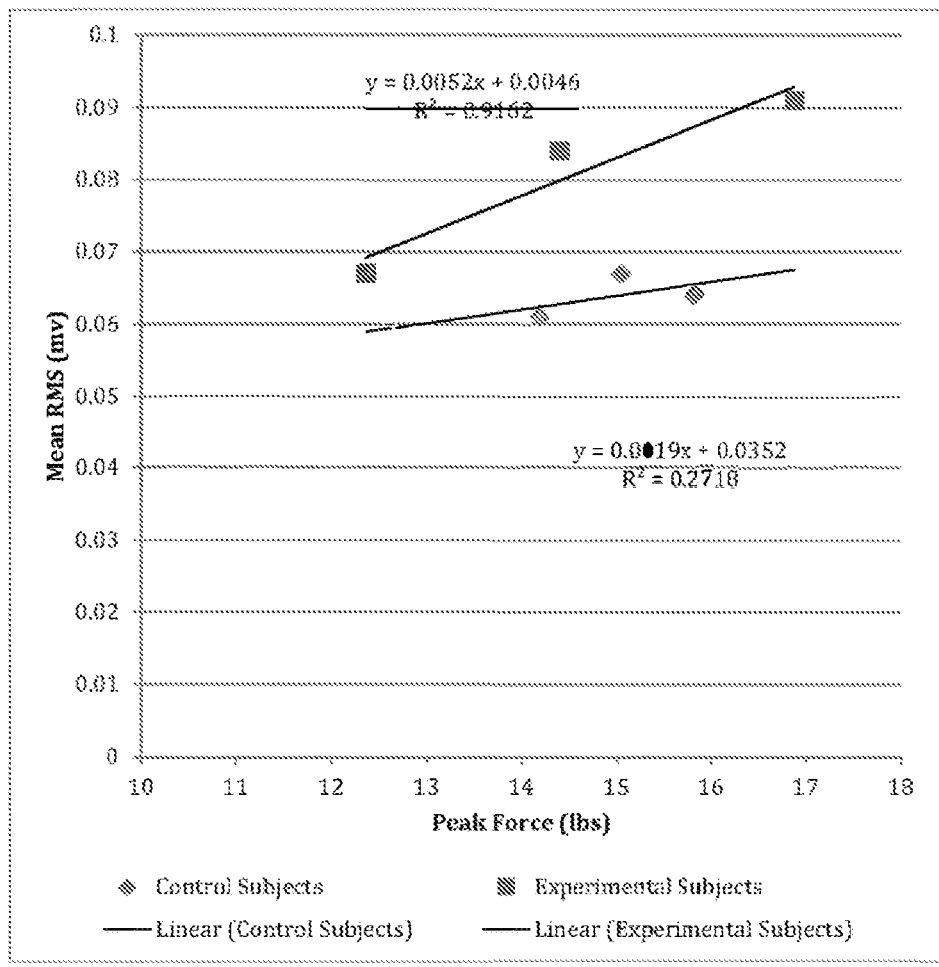
FIG. 13 shows the relationship between the peak force and the mean EMG Root Mean Square for the three test conditions, results from the interim analysis of the Pilot Study described in the Examples section of this disclosure. A reasonable linear relationship was observed for peak force and mean EMG RMS.
Figure 14:
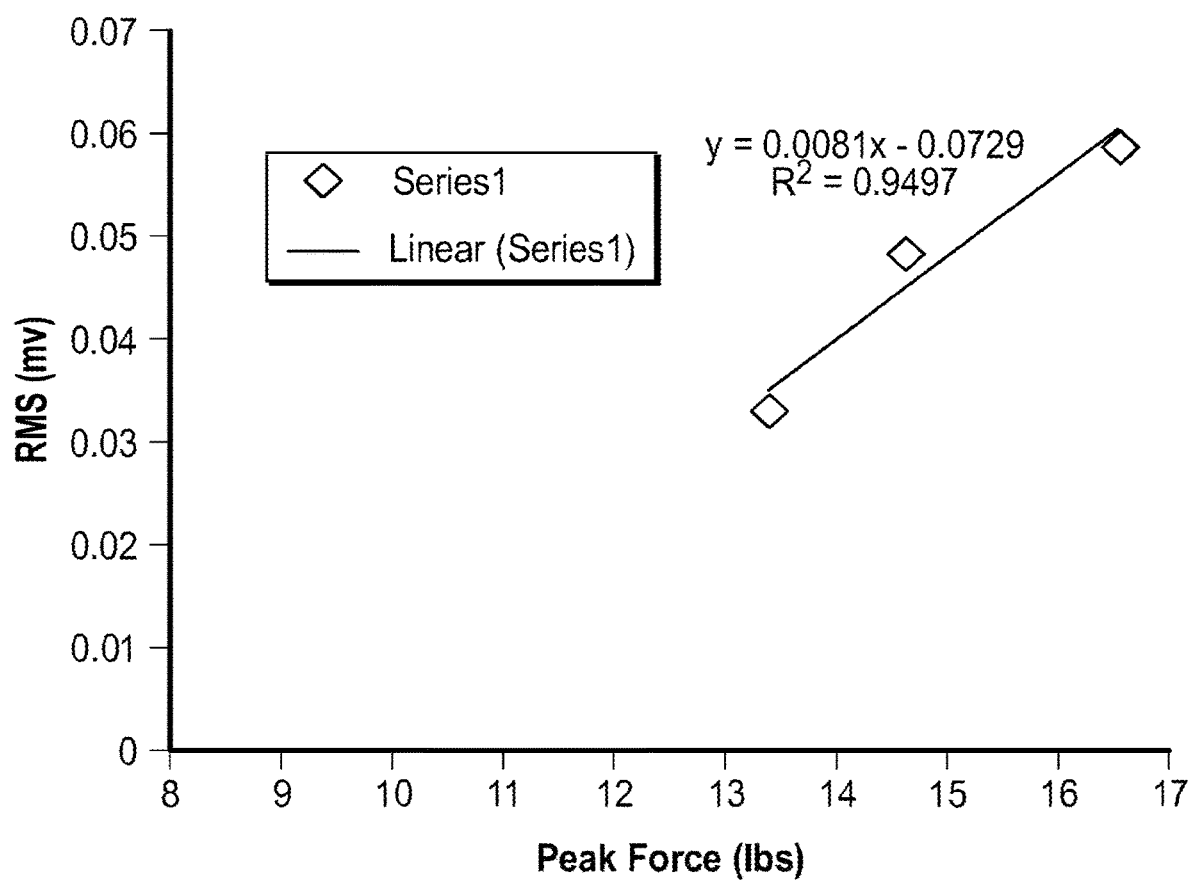
FIG. 14 shows an example of an individual relationship between the peak force and the mean EMG Root Mean Square for the three test conditions, experimental subject, anterior deltoid muscle, wherein results from the interim analysis of the Pilot Study described in the Examples section of this disclosure.

Results: As shown in FIG. 11, with results from n=14 subjects tested in this Pilot Study, a significant difference has been observed in change in peak force between experimental and control subjects ($p<0.05$). The "Chip Applied" data refers to a peak force when a therapeutic device is being applied to a patient, which is contrasted with a pre-treatment peak forces. The "Post 'Treatment'" data refers to a peak force measurement after the therapeutic device has been removed, which is contrasted with the peak force when a therapeutic device is being applied to a patient. Additionally, the threshold represents a meaningful change in force, based upon published literature. As shown in FIG. 12, a significant difference was observed in the mean EMG Root Mean Square for the three test conditions between Chip Applied and Post "Treatment" for experimental Subjects ($p<0.05$). As shown in FIG. 13, a reasonable linear relationship was observed for peak force and mean EMG Root Mean Square (RMS) for the three test conditions. FIG. 14 provides an example of the relationship between the peak force and the mean EMG Root Mean Square (RMS) for the three test conditions in a single experimental subject, anterior deltoid muscle.

In other embodiments of the invention, an additional layer or layers comprise a resonance frequency or resonance frequencies that are used in applications of the device 32. In these embodiments, the additional layer or layers and its resonance frequency or frequencies may be utilized in tandem with the device and its resonance frequency or frequencies, or the additional layer or layers may stand alone. In other words, the device 32 may optionally include additional layer or layers along with a delivery mechanism to generate the therapeutic benefits of the invention.

The size and shape of a carrier layer at least partially determines the resonance frequency of the carrier layer, and the range of frequencies that the carrier layer is capable of generating. For example, when the carrier layer is a crystal, the crystal may comprise a particular cut that influences the crystal's resonance frequency as well as how environmental qualities such as temperature, pressure, and humidity impact the performance of the crystal. Examples of crystal cuts include, but are not limited to, AT, SC, BT, IT, FC, AK, CT, DT, SL, GT, E, 5° X, MT, ET, FT, NT, XY, H, J, RT, SBTC, TS, X 30°, LC, AC, BC, NLSC, Y, X, and combinations thereof.

The material that the carrier layer is made from also at least partially determines the resonance frequency of the carrier layer, and the range of frequencies that the carrier layer is capable of generating. The carrier layer may be comprised of a variety of materials including, but not limited to, piezoelectric crystal, quartz, silicon, plastic, glass, saline solution, mineral solution, synthetic crystal, sapphire, moissanite, natural crystal, gem stone, metal, ceramic, resin, viscous substance, lithium tantalate, lithium niobate, lithium borate, berlinite, gallium arsenide, lithium tetraborate, aluminium phosphate, bismuth germanium oxide, polycrystalline zirconium titanate ceramics, high-alumina ceramics, silicon-zinc oxide composite, dipotassium tartrate, gallium phosphate, langasite, langanite, langanate, leaded glass comprising 18 to 40% lead oxide determined on a weight basis, and doped variants and/or combinations thereof.

In some embodiments of the present invention the additional layer or layers are resonance inert, meaning the layer does not comprise a resonance frequency. These layers may simply provide a substrate for other imprinted layers. For example, a silicon wafer grown by the Czochralski method adds no characteristic resonance frequencies beyond its natural phonon frequencies.

Delivery mechanisms that excite frequency responses via sympathetic resonance utilize electromagnetic or mechanical waves.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure.

The present disclosure, in various aspects, embodiments, and/or configurations, includes components, methods, processes, systems and/or apparatus substantially as depicted and described herein, including various aspects, embodiments, configurations embodiments, sub-combinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and\or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of delivering replicated key frequencies of a resonant frequency pattern and delivering an electromagnetic field frequency, comprising:
   providing a formula sample having a resonant frequency pattern;
   providing an arbitrary waveform generator, a nonlinear element, and a transmitter; generating, by the arbitrary waveform generator, the replicated key frequencies of the resonant frequency pattern of the formula sample;
   combining, by the nonlinear element, the replicated key frequencies of the resonant frequency pattern of the formula sample and an electromagnetic field frequency into a mixed electronic signal; and delivering, by the transmitter, the mixed electronic signal.

2. The method, as claimed in claim 1, wherein: a frequency-based characteristic of the resonant frequency pattern of the formula sample is a nuclear magnetic resonance spectrum of the formula sample, wherein the nuclear magnetic resonance spectrum has a plurality of local peaks that are selected as key frequencies of the resonant frequency pattern of the formula sample.

3. The method, as claimed in claim 1, wherein: a frequency-based characteristic of the resonant frequency pattern of the formula sample is an infrared vibrational spectrum of the formula sample, wherein the infrared vibrational spectrum has a plurality of local peaks that have been frequency-shifted down to frequencies with harmonics at the infrared frequencies, and the plurality of local peaks are selected as key frequencies of the resonant frequency pattern of the formula sample.

4. The method as claimed in claim 1, wherein: the mixed electronic signal combined by the nonlinear element comprises a waveform, wherein the waveform is one or more of a square wave, a pulse wave, and a sawtooth wave.

5. The method as claimed in claim 1, wherein: the nonlinear element is a diode configured to combine the key frequencies and sum and difference frequencies of the key frequencies with the electromagnetic field frequency into the mixed electronic signal.

6. The method as claimed in claim 1, wherein: an electromagnetic field device comprises the arbitrary waveform generator and the nonlinear element, and the mixed electronic signal is an electromagnetic field output that is modulated by the replicated key frequencies of the resonant frequency pattern of the formula sample.

7. A method of delivering replicated key frequencies of a resonant frequency pattern to catalyze a response to therapy, training, exercise, meditation, or mental activity, comprising:
   providing a formula sample having a resonant frequency pattern;
   combining, by a nonlinear element, replicated key frequencies of the resonant frequency pattern of the formula sample and an electromagnetic field frequency into a mixed electronic signal; delivering, by a transmitter, the mixed electronic signal;
   wherein the delivery of the mixed electronic signal catalyzes a response.

8. The method, as claimed in claim 7, wherein: a frequency-based characteristic of the resonant frequency pattern of the formula sample is a nuclear magnetic resonance spectrum of the formula sample, wherein the nuclear magnetic resonance spectrum has a plurality of local peaks that are selected as key frequencies of the resonant frequency pattern of the formula sample.

9. The method, as claimed in claim 7, wherein: a frequency-based characteristic of the resonant frequency pattern of the formula sample is an infrared vibrational spectrum of the formula sample that has been frequency-shifted down to frequencies with harmonics at the infrared frequencies, wherein the infrared vibrational spectrum has a plurality of local peaks, and the plurality of local peaks are selected as key frequencies of the resonant frequency pattern of the formula sample.

10. The method as claimed in claim 7, wherein: the replicated key frequencies of the resonant frequency pattern of the formula sample are generated by an arbitrary waveform generator that generates one or more of a square wave, a pulse wave, and a sawtooth wave.

11. The method as claimed in claim 7, wherein: the formula sample is a composite formula that comprises at least one resonant frequency pattern from at least one of a nutraceutical formula, an oxygen formula, and a hypoxic formula.

12. The method as claimed in claim 7, wherein: an electromagnetic field is applied by an electromagnetic field device that delivers an electromagnetic field simultaneous with the replicated key frequencies of the formula sample.

13. The method as claimed in claim 7, wherein: a non-electromagnetic means is applied, which includes at least one of a pharmaceutical compound, a physical or chiropractic therapy, a homeopathy therapy, an acupuncture therapy, psychological counseling, Qigong medicine, and Ayurvedic medicine.

14. A method of delivering replicated key frequencies of a resonant frequency pattern to catalyze a response to therapy, training, exercise, meditation, or mental activity, comprising:
 providing a formula sample having a resonant frequency pattern;
 imprinting a device with the replicated key frequencies of the resonant frequency pattern of the formula sample, wherein a frequency-based characteristic of the resonant frequency pattern of the formula sample is a nuclear magnetic resonance spectrum of the formula sample; and
 applying the therapy, training, exercise, meditation, or mental activity, wherein the replicated key frequencies of the formula sample from the imprinted device catalyzes a response;
 wherein the therapy training, exercise, meditation, or mental activity is an electromagnetic therapy, which has an electromagnetic field device that delivers an electromagnetic field, and the electromagnetic field and the replicated key frequencies of the formula sample are simultaneously delivered.

15. The method as claimed in claim 14, wherein the nuclear magnetic resonance spectrum has a plurality of local peaks that are selected as key frequencies of the resonant frequency pattern of the formula sample.

16. The method, as claimed in claim 14, wherein: a plasma generator imprints the device with the plurality of key frequencies from the resonant frequency pattern of the formula sample, the plasma generator comprises a vessel that defines an enclosed volume, and the plasma generator strikes an inert gas in the enclosed volume into a plasma state, which imprints the device with the plurality of key frequencies.

17. A method of delivering replicated key frequencies of a resonant frequency pattern to catalyze a response to therapy, training, exercise, meditation, or mental activity, comprising:
 providing a formula sample having a resonant frequency pattern, wherein a frequency-based characteristic of the resonant frequency pattern of the formula sample is an infrared vibrational spectrum of the formula sample,
 imprinting a device with the replicated key frequencies of the resonant frequency pattern of the formula sample;
 applying the therapy, training, exercise, meditation, or mental activity, wherein the replicated key frequencies of the formula sample from the imprinted device catalyzes a response; and
 wherein the therapy training, exercise, meditation, or mental activity is an electromagnetic therapy, which has an electromagnetic field device that delivers an electromagnetic field, and the electromagnetic field and the replicated key frequencies of the formula sample are simultaneously delivered.

18. The method, as claimed in claim 17, wherein: the infrared vibrational spectrum has a plurality of local peaks that have been frequency-shifted down to frequencies with harmonics at the infrared frequencies, and the plurality of local peaks are selected as key frequencies of the resonant frequency pattern of the formula sample.

* * * * *